Figure 1:
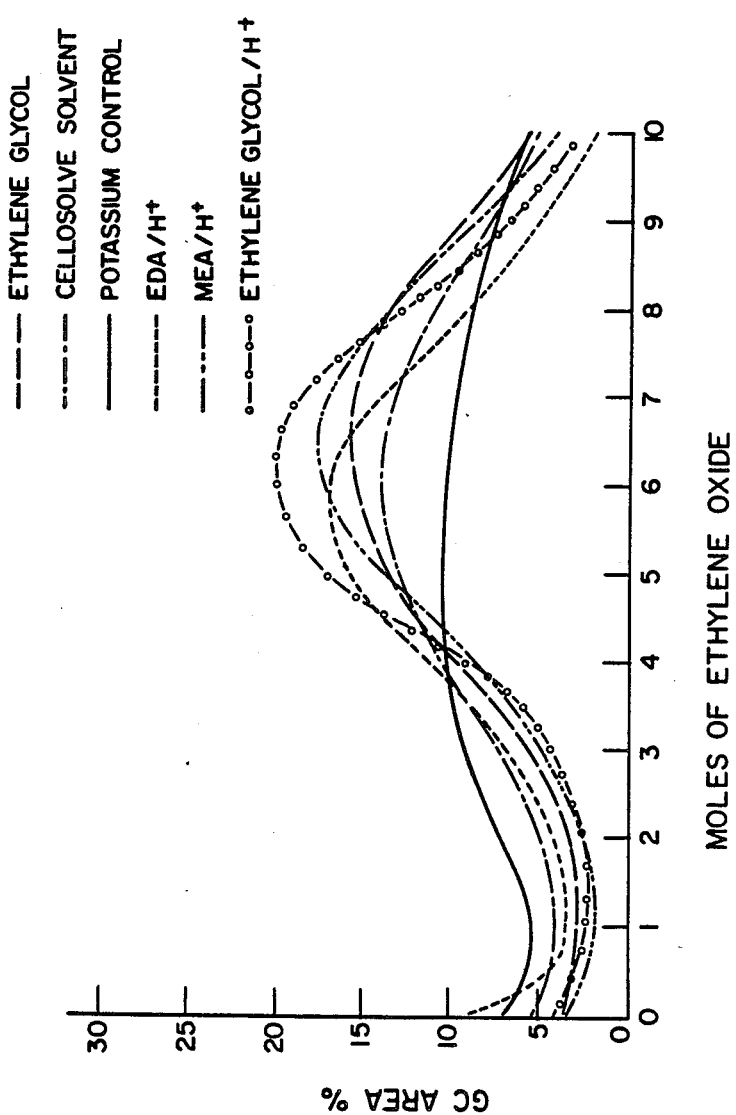

United States Patent [19]

Knopf et al.

[11] Patent Number: 4,886,917

[45] Date of Patent: Dec. 12, 1989

[54] ALKOXYLATION USING CALCIUM CATALYSTS AND PRODUCTS THEREFROM

[75] Inventors: Robert J. Knopf, St. Albans; Louis F. Theiling, Jr., Charleston, both of W. Va.

[73] Assignee: Union Carbide Chemicals and Plastics Company Inc., Danbury, Conn.

[21] Appl. No.: 916,015

[22] Filed: Oct. 6, 1986

Related U.S. Application Data

[60] Division of Ser. No. 621,991, Jun. 22, 1984, abandoned, which is a continuation-in-part of Ser. No. 510,804, Jul. 5, 1983, abandoned.

[51] Int. Cl.$^4$ .................... C07C 43/11; C07C 43/04
[52] U.S. Cl. .................... 568/623; 568/622; 568/624; 568/625; 568/618; 568/620; 568/606; 568/607; 568/608; 568/609; 568/614; 502/155; 252/174.21
[58] Field of Search ............ 568/623, 622, 618, 606, 568/607, 609, 612, 614, 624, 625, 608

[56] References Cited

U.S. PATENT DOCUMENTS

| 4,223,164 | 9/1980 | Yang et al. . |
|---|---|---|
| 4,239,917 | 12/1980 | Yang . |
| 4,396,780 | 8/1983 | Shtykh et al. ................ 568/623 |
| 4,453,022 | 6/1984 | McCain et al. ............... 568/623 |
| 4,453,023 | 6/1984 | McCain et al. . |

FOREIGN PATENT DOCUMENTS

| 0026544 | 4/1981 | European Pat. Off. . |
|---|---|---|
| 0026546 | 4/1981 | European Pat. Off. . |

*Primary Examiner*—Howard T. Mars
*Attorney, Agent, or Firm*—Norman L. Balmer; Gerald L. Coon

[57] ABSTRACT

Narrow, balanced alkoxylation product mixture distributions having at least one alkoxylation product constituting more than 20 weight percent of the mixture can be provided by modified, calcium-containing catalysts. Catalysts for alkoxylation processes can be produced from lime and can, with modification, be used to make the narrow, balanced alkoxylation product mixture distribution.

31 Claims, 4 Drawing Sheets

ALKOXYLATION USING CALCIUM CATALYSTS AND PRODUCTS THEREFROM

This application is a division of prior U.S. application Ser. No. 621,991, filed June 22, 1984, which is a continuation-in-part of application Ser. No. 510,804, filed July 5, 1983, both now abandoned.

This invention relates to the use of calcium-containing catalysts for the preparation of alkoxylation products, i.e., condensation reaction products of epoxides and organic compounds having at least one active hydrogen. In one aspect of the invention, alkoxylation products are provided that have beneficial, narrow molecular weight ranges. These alkoxylation products can be prepared using modified calcium-containing catalysts. In a further aspect of the invention, processes are provided for preparing calcium-containing catalysts for alkoxylation using calcium oxide or calcium hydroxide.

Background to Alkoxylation Products

A variety of products such as surfactants, functional fluids, glycol ethers, polyols, and the like, are commercially prepared by the condensation reaction of epoxides with organic compounds having at least one active hydrogen, generally, in the presence of an alkaline or acidic catalyst. The types and properties of the alkoxylation products depend on, among other things, the active hydrogen compound, the epoxide, and the mole ratio of epoxide to organic compound employed, as well as the catalyst. As a result of the alkoxylation, a mixture of condensation product species are obtained having a range of molecular weights.

In many applications of alkoxylated products, certain of the alkoxylation species provide much greater activity than others. Consequently, alkoxylation processes are desired that are selective to the production of those alkoxylation species. Further, for many of these uses, mixtures of alkoxylation products falling within a narrow range of molecular distribution of reacted epoxide are believed to be superior to alkoxylation products in which a single alkoxylation specie predominates. For example, in a surfactant composition the range of materials on which the surfactant will be required to operate will normally vary. A range of alkoxylation species, even though narrow, will enhance the performance of the surfactant to the variety of materials which it may encounter. Further, mixtures of closely related alkoxylation species can provide a mixture having other improved properties such as in respect to cloud point, freezing point, pour point and viscosity as compared to a single specie. There, however, is a balance, and if the distribution of species becomes too broad, not only are less desirable alkoxylation species diluting the mixture, but also the more hydrophilic or lipophilic components than those in the sought range can be detrimental to the sought properties.

Moreover, a wide range of alkoxylation species can restrict the flexibility in ultimate product formulation using the alkoxylation reaction product. For example, in making oil-in-water emulsion products it is often desired to prepare a concentrated composition that minimizes the weight percent of water. This concentrate may then be diluted with water at the time of use, thereby saving the expense of shipping and storing water. The ability to form a desirable concentrate is generally dependent, in part, on having a narrow distribution of alkoxyltion species since its heavier moieties are present, a greater portion of water is usually required otherwise gelling (evidencing product instability) may occur.

The recognition that certain distributions of moles of epoxide to moles or organic compound in alkoxylation products can be important has long been recognized. For example, British Patent Specification No. 1,399,966 discloses the use of ethoxylates having a hydrophilic-lipophilic balance (HLB) of from about 10 to about 13.5 for use in a laundry detergent. In order to provide this HLB, the moles of ethylene oxide reacted per mole of fatty alcohol is described as being critical. In British Patent Specification No. 1,462,133, the sought cleaning composition employed alkylene oxide cosurfactants sufficient to provide even a narrower HLB, i.e., from about 10 to about 12.5. In British Specification No. 1,462,134, a detergent composition is disclosed which uses ethoxylates having an HLB of from about 9.5 to 11.5, with the preferred ethoxylates having an HLB of 10.0 to 11.1.

Thus, with the increased understanding of the properties to be provided by an alkoxylation product, greater demands are placed on tailoring the manufacture of the alkoxylation product to enhance the sought properties. Accordingly, efforts have been expended to provide alkoxylated products in which the distribution of reacted epoxide units per mole of organic compound is limited to a range in which the sought properties are enhanced.

Alkoxylation Processes

Alkoxylation processes are characterized by the condensation reaction is the presence of a catalyst of at least one epoxide with at least one organic compound containing at least one active hydrogen. Perhaps the most common catalyst is potassium hydroxide. The products made using potassium hydroxide, however, generally exhibit a broad distribution of alkoxylate species. See, for example, M. J. Schick, *Nonionic Surfactants*, Volume 1, Marcel Dekker, Inc., New York, NY (1967) pp. 28 to 41. That is, little selectivity to particular alkoxylate species is exhibited, especially at higher alkoxylation ratios. For example, FIG. 6 of U.S. Pat. No. 4,223,164 depicts the distribution of alkoxylate species prepared by ethoxylating a fatty alcohol mixture with 60 weight percent ethylene oxide using a potassium catalyst.

The distribution that will be obtained in alkoxylation processes can vary even using the same type of catalyst depending upon the type of organic compound being alkoxylated. For example, with nonylphenol, a Poisson-type distribution can be obtained using a potassium hydroxide catalyst. However, with aliphatic alcohols such as decanol, dodecanol, and the like, the distribution is even broader. These distributions are referred to herein as "Conventional Broad Distributions".

Acidic catalysts can also be used, and they tend to produce a narrower, and thus more desirable, molecular weight distributions; however, they also contribute to the formation of undesired by-products and, thus, are not in wide use commercially.

Particular emphasis has been placed on controlling molecular weight distribution of alkoxylation products. One approach has been to strip undesirable alkoxylate species from the product mixture. For instance, U.S. Pat. No. 3,682,849 discloses processes for the vapor phase removal of unreacted alcohol and lower boiling ethoxylate components. The compositions are said to contain less than about 1% of each of non-ethoxylated alcohols and monoethoxylates, less than 2% by weight of diethoxylates and less than 3% by weight of triethoxylates. This process results in a loss of raw materials since the lower ethoxylates are removed from the composition. Also, the stripped product still has a wide distribution of ethoxylate species, i.e., the higher molecular weight products are still present in the composition to a significant extent. To circumvent viscosity problems which would normally exist with straight-chain alcohols, about 20 to 30 percent of the starting alcohol is to be branched according to the patent.

Obtaining a narrower distribution of alkoxylated species at lower epoxide reactant to organic compound mole ratios can be readily accomplished. U.S. Pat. No. 4,098,818 discloses a process in which the mole ratio of catalyst (e.g., alkali metal and alkali metal hydride) to fatty alcohol is about 1:1. Ethoxylate distributions are disclosed for Parts C and D of Example 1 and are summarized as follows:

|  | Part C | Part D |
| --- | --- | --- |
| Primary fatty alcohol | 12 carbons | 12 to 14 carbons |
| Moles of ethylene oxide per mole of alcohol | 3.5 | 3 |
| Product molecular weight | 352 | 311 |
| Average ethoxylation | 3.8 | 2.54 |
| Distribution, % | | |
| $E_0$ | 0.7 | 3.8 |
| $E_1$ | 6.3 | 15.3 |
| $E_2$ | 17.3 | 25.9 |
| $E_3$ | 22.4 | 23.8 |
| $E_4$ | 21.2 | 15.9 |
| $E_5$ | 15.6 | 10.7 |
| $E_6$ | 8.6 | 3.5 |
| $E_7$ | 5.6 | 1.2 |
| $E_8$ | 2.3 | — |

The high catalyst content in combination with the low epoxide to alcohol ratio appears to enable a narrow, low ethoxylate fraction to be produced. However, as the ratio of epoxide to alcohol increases, the characteristic, Conventional Broad Distribution of alkali metal catalysts can be expected. Moreover, even though the disclosed process is reported to provide a narrower distribution of ethoxylate species, the distribution is skewed so that significant amounts of the higher ethoxylates are present. For example, in Part C, over 15 percent of the ethoxylate compositions had at least three more oxyethylene groups than the average based on the reactants, and that amount in Part D is over 16 percent.

European Patent Application No. A0095562, published Dec. 12, 1983, exemplifies the ability to obtain high selectively to low ethoxylate species when low ratios of ethylene oxide reactant to alcohol are employed as well as the tendency to rapidly loose that selectivity when higher ethoxylated products are sought. For instance, Example 1, (described as a 1 mole EO adduct), which reports the use of a diethylaluminum fluoride catalyst, employs 300 grams of a 12 to 14 carbon alcohol and 64 grams of ethylene oxide and Example 5, (described as a 1.5 mole EO adduct) using the same catalyst, employs a weight ratio of alcohol to ethylene oxide at 300:118. Based on the graphically presented data, the distributions appear to be as follows:

|  | Example 1 | Example 5 |
| --- | --- | --- |
| $E_0$ | 27 | 10 |
| $E_1$ | 50 | 36 |
| $E_2$ | 17 | 33 |
| $E_3$ | 4 | 16 |
| $E_4$ | — | 6 |
| $E_5$ | — | 2 |
| $E_6$ | — | 1 |

Even with a small increase in ethoxylation from the described 1 mole EO adduct to the described 1.5 mole adduct, the distribution of ethoxylate species broadened considerably with more of the higher ethoxylates being produced as can be expected from a Conventional Broad Distribution. It may be that the catalyst is consumed in the reaction process so that it is not available to provide the narrower distributions of alkoxylation product mixtures at the high adduct levels.

Several catalysts have been identified that are reported to provide molecular weight distributions for higher ethoxylates that are narrower than those expected from a Conventional Broad Distribution. In particular, this work has emphasized ethoxylation catalysts by derivatives of the Group IIA alkaline earth metals. Interest in these catalysts, which to date has been confined almost exclusively to the production of non-ionic surfactants, stems from their demonstrated capability for providing hydrophobe ethoxylates having narrower molecular weight distributions, lower unreacted alcohol contents, and lower pour points than counterparts manufactured with conventional alkali metal-derived catalysts.

Recently, Yang and coworkers were granted a series of U.S. patents which describe primarily the use of unmodified or phenolic-modified oxides and hydroxides of barium and strontium as ethoxylation catalysts for producing non-ionic surfactants exhibiting lower pour points, narrower molecular weight distributions, lower unreacted alcohol contents and better detergency than counterpart products prepared by state-of-the-art catalysis with alkali metal hydroxides. See U.S. Pat. Nos. 4,210,764; 4,223,164; 4,239,917; 4,254,287, 4,302,613 and 4,306,093. Significantly, these patents contain statements to the effect that the oxides and/or hydroxides of magnesium and calcium do not exhibit catalytic activity for ethoxylation, although they may function in the role of promoters for the barium and strontium compounds (U.S. Pat. No. 4,302,613).

The molecular weight distributions of the ethoxylates disclosed in these patents, while being narrower than conventional distributions, appear not to meet fully the desired narrowness. For example, FIG. 6 of U.S. Pat. No. 4,223,146 depicts the product distribution of an ethoxylate of a 12 to 14 carbon alcohol and 60 percent ethylene oxide using various catalysts. A barium hydroxide catalyst is described as providing a product mixture containing, as the most prevalent component, about 16 percent of the six mole ethoxylate. The distribution is, however, still relatively wide in that the ethoxylate species having three or more oxyethylene groups than the most prevalent component is above about 19 weight percent of the mixture and the distribution is skewed toward higher ethoxylates. The strontium hydroxide catalyst run which is also depicted on that figure appears to have a more symmetrical distribution but the most prevalent component, the seven mole ethoxylate, is present in an amount of about 14.5 weight percent and about 21 weight percent of the composition had three or more oxyethylene groups than the most prevalent component.

Figure 4:
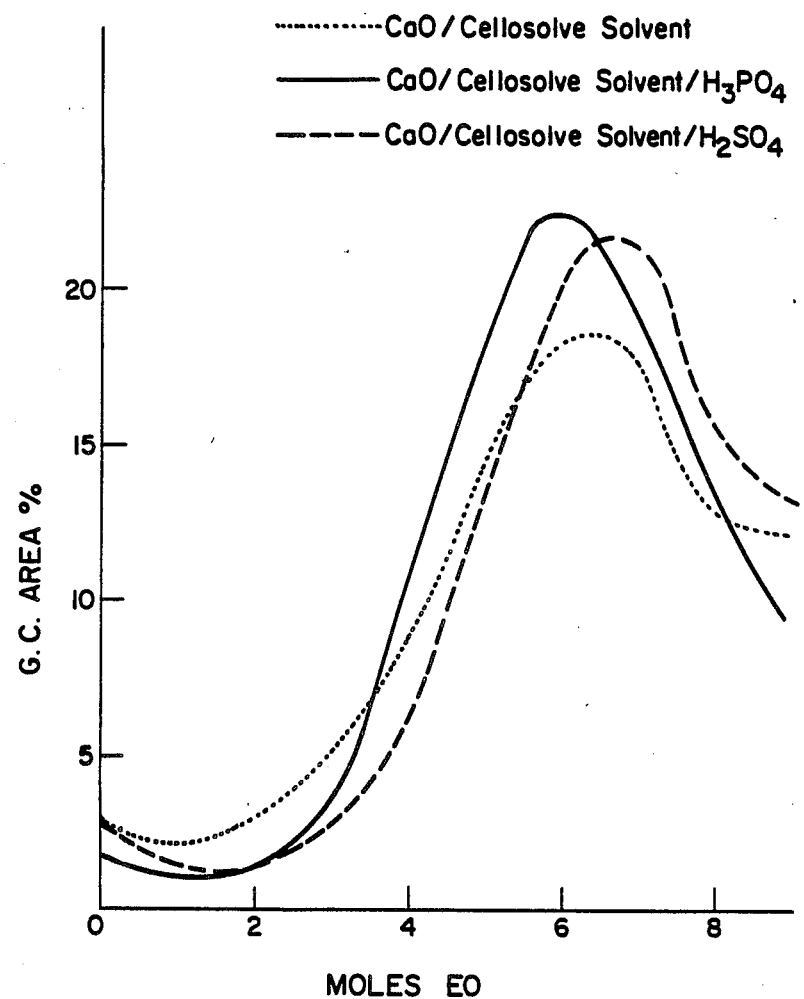

Also, U.S. Pat. No. 4,239,917 discloses ethoxylate distributions using barium hydroxide catalyst and a fatty alcohol. FIG. 7 of that patent illustrates the distribution at the 40 percent ethoxylation level with the four mole ethoxylate being the most prevalent component. Over about 10 weight percent of the mixture has three or more oxyethylene groups than the most prevalent component. FIG. 4 depicts the distribution of ethoxylation at the 65 percent ethoxylation level. The nine and ten mole ethoxylates are the most prevalent and each represent about 13 weight percent of the composition. The distribution is relatively symmetrical but about 17 weight percent of the composition has at least three more oxyethylene groups than the average peak (9.5 oxyethylene groups). Interestingly, comparative examples using sodium hydroxide catalyst are depicted on each of these figures and evidence the peaking that can be achieved with conventional base catalysts at low ethoxylation levels, but not at higher ethoxylation levels.

Introduction to Calcium-Containing Catalysts

McCain and co-workers have published a series of European patent applications describing the catalytic use of basic salts of alkaline earth metals especially calcium, which are soluble in the reaction medium. These applictions further disclose catalyst preparation procedures involving alcohol exchange in respect to the alkoxy moiety of the metal alkoxide catalytic species. See European patent publication No. 0026544, No. 0026547, and No. 0026546, all herein incorporated by reference. See also U.S. Ser. No. 454,560, filed Dec. 30, 1982 (barium-containing catalyst). These workers have also disclosed the use of strong acids to partially neutralize and thereby promote the catalytic action of certain alkaline earth metal derivatives. See U.S. Ser. No. 370,204, filed Apr. 21, 1982, and No. 454,573, filed Dec. 30, 1982 (barium-containing catalyst), both herein incorporated by reference. These workers also tend to confirm Yang's findings as to calcium oxide, in that McCain, et al., teach that calcium oxide does not form a lower alkoxide when treated with ethanol.

In particular, calcium metal or calcium hydride is typically the starting material used by McCain, et al., to make the calcium-containing catalyst. These starting materials, however, are expensive. Consequently, a desire exists to use commonly found sources of calcium, such as calcium oxide (quicklime) and calcium hydroxide (slaked lime), to make calcium-containing catalysts for alkoxylation. Moreover, quicklime and slaked lime are by far the cheapest, most plentiful, least noxious, and most envionmentally-acceptable of all the alkaline earth metal derivatives.

The calcium-containing catalyst disclosed by McCain, et al., provide enhanced selectivities to higher alkoxylate species as compared to mixtures produced using conventional potassium hydroxide catalyst. Indeed, bases exist to believe that these calcium-containing catalysts provide narrower distributions of alkoxylates than those provided by strontium- or barium-containing catalysts. However, there is still need for improvement in providing a narrower yet distribution of alkoxylation products, particularly a distribution in which at least one component constitutes at least 20 weight percent of the composition and alkoxylation products having more than three alkoxyl groups than the average peak alkoxylation component comprise very little of the product mixture.

Summary of the Invention

By this invention, alkoxylation product mixtures are provided which have a narrow, but balanced distribution of alkoxylation species. These product mixtures are relatively free from large amounts of substantially higher alkoxylation moieties, i.e., those having at least three more alkoxyl groups than the average peak alkoxylate specie. Advantageously these narrow distributions can be obtained where the most prevalent alkoxylation moiety has four or greater alkoxy units, that is, in the regions in which conventional catalyst provide a relatively wide range of alkoxylation species.

Another aspect of this invention relates to processes for preparing alkoxylation mixtures having relatively narrow alkoxylation product distributions, including the alkoxylation product mixtures of this invention, using modified, calcium-containing catalysts. And in a further aspect of this invention, processes are provided for making alkoxylation catalysts using calcium oxide and/or calcium hydroxide as sources for the catalytically-active calcium.

The alkoxylation product mixtures of this invention are characterized as the condensation reaction products of epoxides and organic compounds having at least one active hydrogen in which the mole ratio of reacted epoxide per active hydrogen (hereinafter E/H Ratio) is at least about 4, say, about 4 to 16 or 24, preferably about 5 to 12. The product mixtures have at least one alkoxylation moiety which constitutes at least about 20, say, about 20 to 30 or 40, and most often about 20 to 30, weight percent of the composition. The alkoxylation mixtures of this invention also have a relatively symmetrical distribution. Hence, the portion of the product mixture having three or more oxyalkylene unit groups (per active hydrogen site of the organic compound) than the peak alkoxylation specie is relatively minor, e.g., often less than about 12, say, less than 10, and often about 1 to 10, weight percent of the mixture. Similarly, the alkoxylation species having fewer oxyalkylene groups (per active hydrogen site of the organic compound) by three or more oxyalkylene groups from the average peak alkoxylation specie is usually relatively minor, e.g., less than about 15, say, less than about 10, often about 0.5 to 10, weight percent of the composition. Generally, the one oxyalkylene unit higher and the one oxyalkylene unit lower alkoxylates in respect to the most prevalent alkoxylation specie are present in a weight ratio to the most prevalent alkoxylation specie of about 0.6:1 to 1:1.

The preferred alkoxylation product mixtures of this invention correspond to the formula $$P_n = A \times e^{-(n-\bar{n})/2.6 + 0.4\,n}$$

wherein n is the number of oxyalkylene groups per reactive hydrogen site for an alkoxylation specie (n must equal at least one) of the composition, $\bar{n}$ is the weight average oxyalkylene number, A is the weight percent of the most prevalent alkoxylation specie in the mixture and $P_n$ is, within plus or minus two percentage points, the weight percent of the alkoxylation specie having n oxyalkylene groups (per active hydrogen site) in the mixture. This distribution relationship generally applies where n is between the amount of $\bar{n}$ minus 4 to the amount of $\bar{n}$ plus 4.

For purposes herein, the "average peak alkoxylation specie" is defined as the number of oxyalkylene groups (per active hydrogen site) of the most prevalent alkoxylation specie when the next higher and lower homologs are each present in a weight ratio to the most prevalent alkoxylation specie of less than 0.9:1. When one of the adjacent homologs is present in a weight ratio greater than that amount, the average peak alkoxylation specie has an amount of oxyalkylene groups equal to the number average of those of the two species. The "weight average oxyalkylene number" is the weight average of the oxyalkylene groups of the alkoxylation species in the mixture (including unreacted alcohol) i.e., $\bar{n}$ equals the sum of $(n)(P_n)$ for all the species present divided by 100.

The processes of this invention involve the condensation reaction of epoxide and at least one organic compound having at least one active hydrogen in the presence of a catalytically effective amount of a modified, calcium-containing catalyst. The modified catalyst comprises a strong, inorganic oxyacid provided in an amount of about 0.2 to 0.9, e.g., 0.35 to 0.85, often, about 0.45 to 0.75, times that required to neutralize the catalyst composition, which is sufficient to narrow the distribution of the alkoxylation product mixture and provide at least one alkoxylation specie in an amount of at least about 20 weight percent of the mixture. The modified catalyst is prepared under sufficient agitation to ensure a relatively uniform product in which the full oxysalt of calcium (e.g. $CaSO_4$) is not produced to a detrimental extent. The preferred oxyacid is sulfuric acid. Frequently, the modified catalyst is prepared in a medium having a dielectric constant at 25° C. or its normal boiling point, whichever is less, of at least about 10, preferably, at least about 20, say, about 20 to 50, and frequently about 25 or 30 to 45.

Another aspect of the invention provides a method for preparing an alkoxylation catalyst, which method comprises solubilizing, at least in part, calcium oxide and/or calcium hydroxide. The term "solubilizing as used herein is intended to mean that the calcium is provided in an active form which is not the case when calcium is in the form of calcium oxide or calcium hydroxide, hence a solubilization is believed to exist; however, the term is not intended to be limiting to the formation of a truly dissolved calcium specie (which may or may not exist). The solubilization is effected by by mixing any of calcium oxide and calcium hydroxide with an activator having the general formula $Z_a$—X—Q—Y—$Z'_b$ wherein X and Y are the same or different electronegative (relative to carbon), hetero (i.e., non-carbon) atoms selected from the group consisting of oxygen, nitrogen, sulfur and phosphorous; a and b are the same or different integers satisfying the valency requirements of X and Y; Q is any organic radical which is electropositive or essentially netural relative to X and/or Y, which does not prevent the solubilization, and which contains at least one carbon atom and preferably has the formula

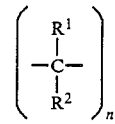

wherein $R^1$ and $R^2$ are the same or different and are selected from the group consisting of hydrogen and lower alkyl or alkylene groups of one to four carbon atoms, and n is an integer from 1 to 6, preferably 2 to 4; Z and Z' are the same or different and are either hydrogen or an organic radical which does not interfere with the function of the activator for its intended purpose, i.e., its solubilizing function, thereby forming an essentially solid catalyst which is catalytically active in the alkoxylation of compounds having active hydrogens, especially alcohols.

Solubilization of calcium oxide or calcium hydroxide results in the production of an alkaline slurry, which alkalinity can be detected and measured by titration and which is referred to herein as "titratable alkalinity".

The catalyst composition can be directly contacted with alkylene oxides to form alkoxylates of the activator itself, if having an active hydrogen, to produce alkoxylates. If the activator does not have an active hydrogen, excess activator should preferably be removed prior to alkoxylation.

According to further embodiments of this aspect of the invention, an exchange reaction is carried out after the reaction of the calcium oxide or calcium hydroxide with the activators under conditions at which an exchange reaction will occur, with at least one organic compound having an active hydrogen, e.g., an alcohol, having a higher boiling point (and usually a longer carbon chain length) than said activator to form the corresponding, catalytically active higher boiling derivative of calcium. This latter catalytic species can then be directly contacted with alkylene oxide to form alkoxylates of the higher boiling material.

In particularly preferred embodiments of the present invention, the calcium-containing composition (containing either the activator or the exchanged, higher boiling material) is contacted with, and partially neutralized by, a strong, preferably oxy-, acid to produce an essentially solid composition which is also catalytically active in the alkoxylation of organic compounds having at least one active hydrogen and provides narrower molecular weight distribution alkoxylates than are obtained with the untreated catalyst. This acid treatment can be performed either before or after any removal of activator.

Discussion of Alkoxylation Product Mixtures

Alkoxylation product mixtures comprise alkoxylation species that can be represented by the formula $$R[(CHR^1-CHR^2O)_n H]_m$$

wherein R is an organic residue of an organic compound having at least one active hydrogen, m is an integer of at least 1 up to the number of active hydrogens contained by the organic compound, $R^1$ and $R^2$ may be the same or different and can be hydrogen and alkyl (including hydroxy- and halo-substituted alkyl) of, for example, 1 to 28 carbons, and n is an integer of at least 1, say, 1 to about 50.

Organic compounds having active hydrogens include alcohols (mono-, di- and polyhydric alcohols), phenols, carboxylic acids (mono-, di- and polyacids), and amines (primary and secondary). Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms.

Particularly preferred alcohols are primary and secondary monohydric alcohols which are straight or branched chain such as methanol, ethanol, propanol, pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenyls of up to 30 carbons such as p-methylphenol, p-ethylphenol, p-butylphenol, p-heptylphenol, p-nonylphenol, dinonylphenol and p-decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

The epoxides which provide the oxyalkylene units in the ethoxylated products include alkylene oxides such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, and 1,2-decylene oxide; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted epoxides such as glycidol, epichlorhydrin and epibromhydrin. The preferred epoxides are ethylene oxide and propylene oxide.

The selection of the organic residue and the oxyalkylene moieties is based on the particular application of the resulting alkoxylation product. Advantageously, narrow distributions can be obtained using a wide variety of compounds having active hydrogens, especially monohydric alcohols, which provide desirable surfactants. Because of the narrow distribution of the alkoxylation product mixture, especially attractive alkoxylation products are surfactants in which certain hydrophilic and lipophilic balances are sought. Hence, the organic compound often comprises a monohydric alcohol of about 8 to 20 carbons and the epoxide comprises ethylene oxide.

While the processes described herein are capable of selectively providing narrow distributions of alkoxylates with the most prevalent having as low as one mole of oxyalkylene per mole of active hydrogen site, a particular advantage exists in the ability to provide a narrow distribution at higher levels of alkoxylation, e.g., wherein the most prevalent specie has at least 4 oxyalkylene units. For some surfactant applications, the most prevalent alkoxylation specie has 6, 7, 8, 9, 10, 11 or 12 oxyalkylene units per active hydrogen site. For many surfactant applications, it has been found that a relatively few species provide the desired activity, i.e., a range of plus or minus two oxyalkylene units. Hence, the compositions of this invention are particularly attractive in that the range of alkoxylation is narrow, but not so narrow that a range of activity is lost.

Moreover, the relatively symmetrical distribution of alkoxylate species that can be provided by this invention enhances that balance while providing a mixture that exhibits desirable physical properties such as cloud point, freeze point, viscosity, pour point and the like. For many alkoxylation mixtures of this invention, the species falling within the range of $\bar{n}$ plus or minus two comprise at least about 75, say, about 80 to 95, sometimes 85 to 95, weight percent of the composition. Importantly, the compositions can be provided such that no single alkoxylation product is in an amount of greater than 50 weight percent of the composition, and, most often, the most prevalent specie is in an amount of 20 to about 30 weight percent, e.g., about 22 to 28, weight percent, to enhance the balance of the composition.

Another class of alkoxylation product mixtures are the polyethylene glycols. For instance, triethylene glycol and tetraethylene glycol find applicatin in gas dehydration, solvent extraction and in the manufacture of other chemicals and compositions. These glycols can be prepared by the ethoxylation of ethylene glycol and diethylene glycol. Advantageous processes of this invention enable ethoxylate product compositions containing at least about 80, say, about 80 to 95, weight percent of triethylene glycol and tetraethylene glycol.

Discussion of Alkoxylation Processes

The alkoxylation product mixtures of this invention are enabled by the use of calcium-containing catalysts that have been modified by strong, inorganic oxyacids sufficient to provide the defined narrow distribution of alkoxylation products. The alkoxylation conditions may otherwise vary while still obtaining a narrower distribution of alkoxylate products.

The acid for modification of the catalyst is preferably a polyvalent acid and contains at least one, most often at least about 2, oxygen atoms that are conventionally depicted as double bonded to the nucleus atom. Such acids include sulfuric and phosphoric acid; however, in general the most narrow distributions are obtained using sulfuric acid.

The amount of acid employed and the manner in which it is introduced to prepare the catalyst can be determinative of whether the desired narrow distribution with at least one alkoxylation specie being present in an amount of at least about 20 weight percent of the composition, is achieved. While not wishing to be limited to theory, it is believed that active catalysts for producing narrow distributions of alkoxylation products comprise a calcium atom in association wit the acid anion in a manner in which the calcium atom is activated. Since, for example, calcium sulfate is inactive as an alkoxylation oatalyst, the association between the calcium atom and acid anion must be different than that forming the neutralized salt. Accordingly, conditions that facilitate such salt formation should be avoided.

In general, at the time of modification, the calcium-containing catalyst may be represented by the formula $Ca(XR^3H)_p$ wherein p is one or two, $XR^3H$ is an organic-containing residue of an organic compound having an active hydrogen, and X is oxygen, nitrogen, sulfur or phosphorous. $R^3$ may thus also contain double bonded oxygen (the organic compound was a carboxylic acid), hetero atom such as oxygen, sulfur, nitrogen and phosphorous (e.g., the organic compound was a glycol, polyamine, ether of a glycol or the like). Frequently, $R^3$ comprises 1 to 20 carbons.

The amount of acid added is in an amount of about 0.2 to 0.9, say, about 0.45 to 0.75, times that required to neutralize the catalyst composition. Frequently, the molar ratio of acid sites (sulfuric acid has two acid sites and phosphoric acid has three acid sites) to calcium atoms is about 0.5:1 to 1.8:1.

The acid appears to enable the desired catalytically active calcium species to form; however, it has been found that depending upon other conditions during the neutralization, different amounts of neutralization will provide the optimum catalyst in terms of selectivity and reaction rate during an alkoxylation process. As shown in Example 7, the run wherein the neutralization level of 84.8 percent was employed (Run 7), the highest selectivity to triethylene glycol and tetraethylene glycol was obtained. In Example 8, diethylene glycol rather tha ethylene glycol was used as the medium during the neutralization, and the dependence of selectivity on the degree of neutralization is less pronounced and Run 1 with a neutralization level of 74.7 percent provided the optimum selectivity. Note also that the reaction rate appears to increase with increased degree of neutralization in the case of the diethylene glycol medium in Example 8, (compare Runs 1 and 17) but decrease with increased degree of neutralization in the case of the ethylene glycol medium in Example 7 (compare Runs 5, 7 and 9). Accordingly, an aspect of the invention is providing a level of neutralization sufficient to achieve the narrow distribution of alkoxylate product mixtures.

The medium containing the calcium catalyst can also affect whether the resulting modified calcium catalyst enables the desired narrow distribution of alkoxylation products to be formed. If the medium comprises as the predominant component, i.e., solvent, a material that has a low dielectric constant, the acid can form a separate liquid phase and increased difficulty in obtaining an intimate admixture may be observed. On the other hand, with solvents that are too polar, the organic moiety in association with the calcium atom may be displaced with the solvent. Accordingly, undue amounts of water are typically avoided during the modification of the calcium-containing composition. Most often, the medium and the organic compound providing the moiety on the calcium atom are the same. Particularly convenient media include ethylene glycol, propylene glycol, diethylene glycol, glycerol, butanediols, 1,3-propanediol, and the like. Conveniently, the medium employed, if not intended to be a reactant for producing alkoxylates, should have a sufficiently low boiling point that can readily be removed from the catalyst and organic compound reactant mixture by distillation. Most often, the medium comprises a solvent having at least two hetero-atoms such as the activators described herein.

The acid is preferably added while the calcium-containing composition is being vigorously agitated to avoid undue formation of the neutralized salt. In this regard, a slow addition of the acid to the calcium-containing composition is preferred. Generally, less than 10 percent of the acid to be added is added to the calcium-containing composition at any one time. The addition of the acid can be conducted at a convenient temperature. e.g., about 10° C. to 160° C., say, about 50° C. to 150° C. Preferably, a nitrogen atmosphere is advantageous.

The calcium-containing composition having at least one substituent of the formula —(XR$^3$H) may be prepared in any suitable manner. For example, calcium metal, hydride or acetylide may be reacted with the organic compound containing an active hydrogen atom of the formula HXR$^3$H. With compounds having higher molecular weights, e.g., 4 or more carbons, it is generally preferred to use a lower molecular weight and more reactive and volatile compound of the formula HXR$^3$H (e.g., of 1 to about 3 carbons, especially compounds such as ethanol, ethylamine, ethylene glycol and the like) and then exchange that substituent with the higher molecular weight substituent while removing the lower molecular weight material by volatilization. Alternatively, the calcium-containing composition can be prepared from quicklime or slaked lime by the process disclosed later herein.

The compounds having the formula HXR$^3$H include those organic compounds having active hydrogens described in connection with the alkoxylation products of this invention, such as alcohols, phenols, carboxylic acids and amines. Most often, the compounds having the formula HXR$^3$H are alcohols. When an exchange reaction is to be conducted to provide a higher molecular weight substituent on the calcium atom, it is generally preferred to conduct the acid modification prior to exchange and use a lower molecular weight material for the replacement substituent to enhance the acid modification process.

The preparation of the substituted calcium catalyst composition from calcium metal, hydride or acetylide is typically conducted at elevated temperature, e.g., from about 30° C. to 200° C. or more and in a liquid medium. The organic compound which provides the substitution is normally provided in excess of that required for reaction with the calcium reactant. Hence, the weight ratio of calcium to the organic compound frequently is within the range of about 0.01:100 to 25:100. The reaction may, if desired, be conducted in the presence of an inert liquid solvent. The exchange reaction is also conducted under elevated temperature and, optionally, under reduced pressure to facilitate removal of the more volatile components. Temperatures may range from about 50° C. to 250° C., say, about 80° C. to 200° C. or 250° C., and pressures (absolute) are often in the range of 1 millibar to 5 bars, e.g., about 10 millibars to 2 bars.

It is usually desired that the organic substituent on the modified, calcium-containing catalyst composition correspond to the "starter" component for the alkoxylation process. The starter component is the organic compound having the at least one active hydrogen with which the epoxide reacts.

The alkoxylation is conducted using a catalytically-effective amount of the calcium-containing catalyst, e.g., about 0.01 to 10, often about 0.5 to 5, weight percent based on the weight of the starter component. The catalysts substantially retain their activities during the alkoxylation, regardless of the amount of epoxide employed. Thus, the amount of catalyst can be based on the amount of starter provided to the alkoxylation zone and not the degree of alkoxylation to be effected. Moreover, the catalyst can be recovered (since it is a solid) from the reaction product and reused. Indeed, it has been found that conditioned (preused) catalysts may provide superior products. The catalysts also appear to be relatively storage stable and are relatively tolerant of water. Hence, storage can be effected under convenient conditions.

Normally, the catalyst and the starter component are admixed and then the epoxide is added at the reaction temperature until the desired amount of epoxide has been added, then the product is neutralized and can be finished, if desired, in any procedure including stripping unreacted starter material from the product mixture, filtration, or further reaction, e.g., to form sulfate.

The temperature of the alkoxylation is sufficient to provide a suitable rate of reaction and without degradation of the reactants or reaction products. Often, the temperatures range from between about 50° C. and 270° C., e.g. from about 100° C. to 200° C. The pressure may also vary widely, but when low-boiling epoxides such as ethylene oxide and propylene oxide are employed, a pressurized reactor is preferably used.

The alkoxylation reaction medium is preferably agitated to ensure a good dispersal of the reactants and catalyst throughout the reaction medium. Also, the epoxide is usually added at a rate approximating that which it can be reacted.

While typically alkoxylation products are neutralized, upon removal of the catalysts employed in accordance with the processes of the invention, the alkoxylation product mixture is relatively neutral (e.g., about a pH of 6) regardless of the pH of the catalyst-containing product. Neutralization, however, may assist in the recovery of the catalyst from the alkoxylation product mixture. When neutralizing, acids that may tend to form catalyst-containing gel structures or solids that clog filtering apparatus should be avoided. Conveniently, sulfuric acid, phosphoric acid, propionic acid, benzoic acid and the like are used.

The Manufacture of Catalyst From Lime

The present invention provides a procedure whereby calcium oxide (quicklime) and its hydrated form, calcium hydroxide (slaked lime) (both herein referred to as "lime"), can be effectively used to prepare catalytic species which are active in the alkoxylation of organic compounds having at least one active hydrogen such as alcohols, especially long-chain fatty alcohols, carboxylic acids, amines, polyols and phenols. This is accomplished by the following general procedure.

Lime is first contacted with an "activator" under conditions at which the lime and the activator will react or interact to form one or more catalytically active derivatives, hereinafter referred to collectively as "the derivative". The activator may be any compound having the formula $$Z_a-X-Q-Y-Z'_b$$

wherein the various terms are as previously defined. The derivative of this reaction is especially effective in the alkoxylation of alcohols, particularly primary alcohols such as the long-chain fatty alcohols, or mixtures thereof, which are used as starters in the manufacture of nonionic surfactants. However, the derivative can also be effectively used in the catalytic reaction of a wide variety of organic compounds containing active hydrogen. If, for example, the activator is ethylene glycol, the derivative can readily be utilized in situ to catalyze the alkoxylation of ethylene glycol itself, thereby producing ethylene glycol-started poly(alkylene glycols) of any desired nominal molecular weight and advantageously having a relatively narrow molecular weight distribution.

If, by way of further example, the activator is the monoethyl ether of ethylene glycol (MEEG) and the derivative is directly alkoxylated with ethylene oxide, the product will be a mixture of ethoxylates of MEEG whose composition will be determined by the molar ratio of ethylene oxide to MEEG.

As used herein, the term "excess activator" means that amount of activator which is not chemically or physically bound to calcium and thus can be removed by simple physical means. The technique employed for this operation is not critical. Vacuum stripping is recommended for its simplicity and efficiency, but evaporation and other known procedures may also be used.

The derivative will be obtained as a finely divided, particulate solid, in slurry form, which can be readily separated from the reaction mixture by filtration, decantation, or similar procedures. The product so obtained is catalytically active in alkoxylation reactions, whether or not acid modified.

It is a particularly desirable feature of this invention that the catalyst can be used to provide alkoxylate surfactants having a uniquely narrow molecular weight distribution, low pour point, and low level of unreacted starter component. In this usage, the catalyst is contacted with the starter component, e.g., alcohol, under conditions at which reaction will occur, to perform an alcohol-exchange (which can also be referred to as an alkoxide exchange) reaction. A portion of the starter alcohol thus is present as an alcoholate of calcium, which alcoholate is itself an active species for the alkoxylation reaction. This reaction mixture is then reacted with one or more epoxides, e.g., alkylene oxides such as ethylene oxide, according to known procedures to produce the desired surfactant.

Referring now to the structural formula given above for the activator, X and Y are preferably more than one carbon removed from each other, e.g., in the beta position relative to each other, and are preferably oxygen, as in ethylene glycol, or oxygen and nitrogen, as in monoethanolamine; however, X and Y can also be sulfur or phosphorous. Exemplary of other useful compounds are ethylenediamine, N-methylethanolamine, tetrahydrofurfuryl alcohol, 2-mercaptoethanol, 1,2-propylene glycol, 2-methylthioethanol, 2-ethoxyethanol, diethylene glycol, 1,3-propanediol and 1,4-butanediol.

Z and Z' are the same or different radicals, optionally substituted, and often at least one of Z and Z' is selected from the group consisting of hydrogen, lower linear or branched alkyl of one to four carbon atoms, alkylene from two or about six carbon atoms, phenyl or lower alkyl-substituted phenyl, cycloalkyl of three to about six carbon atoms and alkylene or hetero-atom-substituted alkylene rings.

In the activator, Q may comprise a carbon chain of up to six carbons between X and Y. A two- to four-carbon chain is preferred, however, because the activating capacity of X and Y is maximized at such chain lengths. Of these, a two-carbon chain length is especially preferred. In highly preferred embodiments, Q will be a two-carbon chain and the structural formula will be as follows:

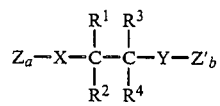

wherein $R^1$, $R^2$, $R^3$, and $R^4$ are preferably hydrogen, but may also be lower alkyl or alkylene groups of one to four carbon atoms, optionally substituted, or such other radicals as do not interfere with the usefulness of the activator for its intended purpose.

Also, Q may be cyclic, preferably cycloalkyl of six or fewer carbons, optionally substituted, as can be represented by the formula:

Compounds coming within this description would include 4-methoxycyclohexane 1,2-diol; 2-aminocyclopentanol; and 2-methoxycyclopentanol.

Similarly, either X or Y or both of them could be part of a ring structure with a carbon atom adjacent to either of them, as illustrated by the formula:

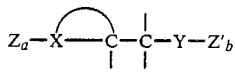

Some compounds illustrating such configurations would include tetrahydrofurfuryl alcohol; furfuryl alcohol; 2-hydroxyethyl aziridine; 1-(N-methyl-2-pyrrolidinyl) ethanol; and 2-aminomethylpyrrolidine.

Moreover, X and Y can themselves be part of the same ring structure, including Q, according to the formula:

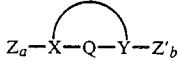

Exemplary of such compounds would be piperazine; 4-hydroxymethyl-2,2-dimethyl-1,3 dioxolane; 2,6-dimethylmorpholine; and cyclohexanone ethylene ketal.

Numerous other ring structures, whether saturated or unsaturated, substituted or unsubstituted, are also possible and are intended to be within the scope of the present invention.

The only perceived limitation on Q and on the overall structure of formula (I) is that the activator must be capable of solubilizing, at least in part, CaO and/or Ca(OH)$_2$. The solubilization of the normally insoluble CaO and Ca(OH)$_2$ is considered to be the threshold step which permits these heretofore inoperable materials to be successfully utilized. Without intending to be bound to any particular theory, this solubilization is believed to be accomplished through the electronwithdrawing effects of hetero-atoms X and Y in relation to adjacent carbon atoms, thereby increasing the acidity of the activator molecule and also helping it to participate in the formation of complexes with calcium, such as exemplified by the structure:

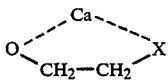

Thus, any structure represented by the formula

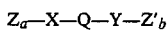

$Z_a$—X—Q—Y—$Z'_b$ is satisfactory, provided only that it does not eliminate or neutralize the electronegativity of the hetero-atoms and thus prevent the activator from performing its intended purpose of solubilizing, at least in part, the CaO and/or Ca(OH)$_2$.

As lime is solubilized, the alkalinity of the medium increases; thus, the "building" of alkalinity can be used as a screening technique to identify potentially useful activators. In this test, one should look for approximately one or more grams of alkalinity, calculated as CaO, based on 5 grams of calcium (calculated as CaO) charged, as determined by titration with 0.01N HCl in ethanol (alcoholic HCl), as will be described more fully below. It should be noted, however, that amines interfere with this test, thus, it cannot be dependably used with amine-containing activator candidates.

Step 1: Catalyst Preparation

In the initial step of the process of this invention, as has been mentioned above, CaO and/or Ca(OH)$_2$ are mixed with the activator to form one or more derivative species. The purpose of this treatment is to solubilize sufficient lime to be catalytically effective in an alkoxylation reaction; thus, the lime concentration could be either below or above its solubility maximum in the activator, provided only that sufficient lime is solubilized to be catalytically effective. As a general guideline, however, the concentration of lime used in the initial step should typically be in the range of about 1-2%, based on the activator. The lime should normally be present somewhat in excess of its solubility in the activator, but lime concentrations exceeding about 30% would rarely be considered desirable.

The temperature for this procedure is not considered critical, and can range from about 50° C. up to the boiling point of the activator, typically well over 200° C. It is desirable to operate in the range of about 90° to 150° C., preferably about 125° to 150° C., and the system can be put under either vacuum or pressure to maintain any desired temperature while maintaining the activator in the liquid phase. Advantageously, the conditions of temperature and pressure are such that water can be vaporized and removed from the reaction medium. Preferably the catalyst preparation is conducted under a substantially inert atmosphere such as a nitrogen atmosphere.

To perform this first step of the process, lime is simply added to the activator in a stirred vessel under sufficient agitation to create a slurry of the lime for a period of time adequate to solubilize at least a portion of the lime. Normally, this will be accomplished within a period of about 1 to 4 hours. The amount of lime which will be solubilized will depend, of course, on the concentration of lime present, the effectiveness of the activator used, and on the temperature, time and agitation employed. Ideally, the quantity of lime desired for the subsequent alkoxylation reaction is solubilized. The source of the lime for this step includes any commercially-available grade of quicklime or slaked lime, since the impurities typically contained in such lime do not significantly adversely affect the catalyst formed by the procedures of this invention.

The resulting lime/activator derivative is suitable for use directly as a catalyst in alkoxylation reactions (although it is preferably acid modified to enhance the narrowness of the alkoxylation product). This would be the case where, for example, ethylene oxide is to be added to the material used as the activator, e.g., ethylene glycol, to produce polyethylene glycols of any desired molecular weight.

If the catalyst is to be used to produce a surfactant or other alkoxylation product using a different starter, an exchange can be performed as described above. For example, in producing a surfactant, the lime/activator derivative can be added to a stirred vessel containing a surfactant range alcohol or mixture of such alcohols, typically $C_{12}$–$C_{14}$ alcohols. The concentration of derivative used can vary over a very broad range, but ideally would be approximately that desired for the subsequent alkoxylation reaction. The temperature during the exchange reaction may be any temperature at which the reaction will occur, but, preferably, will be in the range of about 200°–250° C., and pressure may be adjusted to achieve these temperatures. If the exchange procedure is followed, the activator chosen should have a boiling point of less than about 200° C. to permit it to be readily stripped from the detergent alcohol, most of which boil in the 250° C. range or higher. The resulting alcohol-exchanged product is suitable for use directly as a catalyst in alkoxylation reactions to produce surfactants started with the exchanged alcohol or ,alcohols although it is preferably acid modified to enhance the narrowness of the alkoxylation product.

The catalyst produced by the above-described process is often in the form of a stable slurry of finely divided (e.g., about 5 microns) particles, strongly basic (pH about 11–12), and containing excess CaO.

Step 2: Acid Modification of Lime Derived Catalysts

Although not required for alkoxylation reaction, it is highly preferred that the lime/activator derivative, or the alcohol-exchanged product thereof, be partially neutralized with acid prior to use as catalyst for alkoxylation if narrower distribution of alkoxylate products is desired. While the precise chemical nature of this procedure is not fully understood, it does result in a demonstrable improvement to the overall process in that the molecular weight distribution is narrowed still further. In addition, acid modified catalysts tend to required little or no induction period in the alkoxylation reaction, and also increase that reaction rate over that of their unmodified counterparts. In contrast, addition of acid to conventional catalysts, such as potassium hydroxide, slows the alkoxylation rate while producing no beneficial effect on the product distribution.

Useful acids are the polyvalent, oxyacids of Groups VA and B, VIA and B and VIIB elements, wherein the oxyanion has a valence greater than one. Preferred oxyacids are sulfuric, phosphoric and molybdic and tungstic acids; of these, sulfuric acid is especially preferred. The acid added may be in concentrated or dilute form, although the concentrated form is preferred in order to minimize the amount of water present. The acid may be added to the catalytically active reaction mixture at any time prior to the alkoxylation, and may simply be stirred gradually into the reaction mixture slurry. The acid may be added under whatever ambient conditions prevail, although it is preferred that the slurry be cooled to about 75° C. or less prior to addition of the acid. Neutralization will often occur without significant effect on the physical characteristics of the slurry. Often about 20 to 90%, say, about 25 to about 75%, and sometimes about 40 to about 60%, of the titratable alkalinity of the slurry will be neutralized. Higher degrees of neutralization can be used, but care should be taken not to form the full calcium salt of the oxyanion. In no event should more acid be used than there are equivalents of lime available to react with it. The point in the process at which the acid is added does not appear to be critical.

Advantageous results can be obtained if the catalyst is used in its "crude" form, i.e., without separation from its reaction mixture or purification. Nevertheless, if desired, the lime/activator derivative, whether acid-modified or not, can be separated from its reaction mixture, purified, dried and stored. Such may be accomplished in a straightforward manner, as by stripping off the excess activator or other organic material containing active hydrogen, filtering the resulting slurry, re-slurrying the wet solids with a solvent (e.g., tetrahydrofuran) and refiltering, and drying, preferably under vacuum. The solids thus obtained will be catalytically active, but, frequently, they are substantially less active than the catalyst in its "crude" form. Reaction rate notwithstanding, however, the desired narrow molecular weight distribution and other benefits can still be obtained.

It is a highly desirable, and quite unexpected, benefit of this aspect of the invention that the overall process embodied in the various procedures described above for making catalysts from lime is remarkably "forgiving" of process variations. Thus, as already noted, considerable flexibility exists as to the point acid is added and, within reasonable limits, how much acid is used. Similarly, the unreacted activator may be removed wholly or partially prior to, e.g., an exchange reaction, if used, or it may be left present during the exchange reaction. Moreover, the catalyst may be re-used indefinitely, used and stored in its "crude" form, or purified and dried, with any loss in reaction rate made up by increasing temperature.

The procedures involved in carrying out the process of this invention are illustrated by the following description directed toward the manufacture of nonionic surfactants.

The manner in which the process of this invention is practiced can be illustrated by the following generalized procedure for preparing a slurry of calcium alkoxylation catalyst intended for use in the manufacture of "peaked" (narrow molecular weight distribution) linear alcohol ethoxylates (nonionic surfactants).

As supplied to the specific case of the production of nonionic surfactants, the process of this invention is characterized by a considerable degree of operational latitude. This is particularly true in the preferred version of the process wherein the acid-modified form of the catalyst is produced. From the standpoint of the chemistry which takes place, there are two distinct steps in the preparation of the unmodified catalysts and three distinct steps in the preparation of the acid-modified catalysts. Steps 1 and 2, which are common to the preparation of both catalyst types, involve the following reactions:

Step 1—Reaction of lime (or mixtures of major quantities of lime with minor quantities of other alkaline earth bases) with a suitable activator.

Step 2—Reaction of the product formed in step 1, above, with a detergent range alcohol to effect exchange of the activator-derived organic radicals for detergent-range alcohol-derived organic radicals.

During or following the exchange reactions of step 2 the activator, which preferably is substantially more volatile than the detergent-range alcohol, is removed from the system by distillation. At the conclusion of this operation, the unmodified version of the catalyst is obtained in the form of an activator-free slurry in the detergent-range alcohol.

In the preparation of the unmodified form of the calcium catalyst, steps 1 and 2, above, may be combined into one operation wherein the lime is reacted with a mixture of activator and detergent-range alcohol. In cases where especially effective activators are being used (e.g., ethylene glycol, 1,2-propylene glycol, ethylene glycol monethylether, etc.), this alternative procedure of combining the activator with the detergent-range alcohol is frequently preferred because it tends to minimize color build-up in the catalyst slurry. From the standpoint of the final product characteristics, both procedures are equally acceptable. Modified processes wherein the activator is fed into a slurry of the detergent-range alcohol and the calcium base or the detergent-range alcohol is fed into a slurry (or, in some cases, a solution) of the calcium base in the activator are also operationally viable, although their use offers no perceived advantage over the batch-charging version.

The preparation of the acid-modified catalyst involves a third major processing operation which, like that of steps 1 and 2, is a distinct step in terms of the chemistry which takes place.

Step 3—Treatment of the slurry of unmodified catalyst in detergent-range alcohol with a deficiency of some appropriate polyvalent oxyacid (e.g., $H_2SO_4$, $H_3PO_4$, $H_2MoO_4$, etc.).

This step provides a highly-active, acid-modified calcium catalyst in the form of a slurry in the detergent-range alcohol. Water is believed to be formed as a by-product of this partial neutralization reaction; accordingly, the product slurry is normally subjected to an in vacuo drying operation before it is employed in an ethoxylation reaction to manufacture a nonionic surfactant. The acid modifier charge can be based either upon the initial lime charge or, more desirably where possible, upon an "active catalyst" value which is obtained by titrating a sample of the lime/activator reaction mixture for alkalinity content using 0.01N alcoholic HCl in the presence of bromothymol blue indicator. A particularly convenient procedure is to follow the course of the lime/activator reaction by titration and to base the acid modifier charge upon the alkalinity value obtained when a constant level of alkalinity has been reached. An especially convenient and effective procedure, for example, is to add the acid modifier at a level of about 50% of this "constant" alkalinity value. Monitoring of the lime/activator reaction by titration and ultimately determining the acid modifier charge based upon this analysis, although frequently a preferred procedure, it cannot be used with amino-functional activators because the amine functionality interferes with the alkalinity analysis. In such instances, the preferred procedure is to base the acid modifier charge on the alkalinity value obtained by titrating the activator-free (stripped) slurry of catalyst in detergent alcohol.

The acid modifier may, in most cases, optionally be added at the start of or during the lime/activator reaction, at the start of or during the activator stripping operation, at the conclusion of the activator stripping operation, or even just prior to the start of the alkoxylation reaction itself. In the case of amino-functional activators, of course, the modifiers cannot be added until all the activator has been removed from the slurry.

General Procedure for Process Operation

Because of the fact that this process offers such wide operational latitude, there is no single procedure which can be said to represent the "general procedure." This consideration notwithstanding, one procedure which will suffice to illustrate the process is that version which was used for carrying out many of the preparations summarized in Table I.

Lime (as commercially supplied or calcined 6 hours at 600° C.) and 2-ethoxyethanol (available from Union Carbide) are charged to a suitably-sized, agitated vessel equipped with a reflux condenser, thermocouple, 10-tray distillation column, and inert gas purge inlet. The reactants are charged in weight ratios ranging from 60 to 80 parts of 2-ethoxyethanol to one part of lime. The charge is heated under a nitrogen purge for a period of 2 to 6 hours at the reflux temperature (about 135° C.) while refluxing solvent is removed overhead continuously or intermittently at a make rate sufficiently slow such that during the entire reaction period only about 10 to 15% of the original solvent charge is removed overhead. The purpose of this operation is to remove from the system water which was either introduced with the reactants or produced by chemical reaction. During the reflux period, the reaction mixture is sampled at periodic intervals to monitor the buildup of "alkalinity" which is indicative of the formation of catalytically active materials. The analytical method used for this purpose is a titration with 0.01N HCl in 2-ethoxyethanol using bromothymol blue indicator. When similar "alkalinity" levels are obtained from two successive titrations, the lime/activator reaction step is considered to be finished. The usual timed period to reach this point is about 4 hours under the conditions typical of the runs shown in Table I.

At this point the reaction mixture is diluted with the detergent range alcohol to be ethoxylated; typically the quantity of alcohol added is about 100 g./g. of lime (calculated as CaO) used in the initial reaction. The resulting mixture is cooled to about 75° C. and treated, under agitation, with sufficient acid modifier, preferably sulfuric or phosphoric acid, to neutralize about 50% (on an equivalents basis) of the alkalinity indicated to be present by the final titration performed on the lime/activator reaction mixture.

The temperature is then increased to permit removal of the activator from the reaction mixture by distillation at atmospheric pressure. Distillation at atmospheric pressure is continued until the kettle temperature reaches about 175° to 180° C. At this point the pressure on the system is reduced to about 180 mm Hg and stripping of the activator is continued until the kettle reaches a temperature of about 215° to 225° C. and both the kettle product and the distillate are free of activator as indicated by gas chromatographic (GC) analysis (e.g., less than 1000 ppm by weight and often less than 100 ppm by weight).

The thus-obtained activator-free slurry of catalyst in detergent alcohol can either be used directly as a charge to the ethoxylation reactor or, optionally, diluted with sufficient, dry detergent-range alcohol to afford any desired catalyst concentration in the slurry. A final "alkalinity" value on this slurry may, if desired, be obtained by the same titration procedure described earlier.

The above procedure represents but one of many equally viable versions of this process. The runs summarized in Table I illustrate the use of several, but by no means all, of the versions which are possible through different combinations of the options available in the various process steps.

EXAMPLES

The invention is further illustrated by the following examples, which in no way are intended to limit the applicability or scope of the invention.

Example 1

The general procedure described above was used under a variety of reaction conditions to produce a nonionic surfactant "started" with either 1-dodecanol or one of two commercially available mixtures of $C_{12}$–$C_{14}$ linear, fatty alcohols. The data for these runs are presented in detail in Table I. Referring to Table I, "Alfol" 1214 and "Lorol" 1214 are mixtures of $C_{12}$ and $C_{14}$ alcohols in approximately 55/45 and 70/30 weight ratio, respectively, commercially available from Conoco, Lake Charles, LA, and Henkel Corp. Dusseldorf, W. Germany, respectively. MEEG (available from Union Carbide Corporation, Danbury, Conn. as Cellosolve ™ solvent), was used as the activator. In some runs, marked by an aserisk in the CaO row, the CaO was calcined to drive off all water. In all runs the MEEG was stripped off prior to ethoxylation (e.g., to less than about 100 ppm by weight). In some runs the $H_2SO_4$ modifier was added prior to stripping off the activator, and in some runs, after stripping. Run No. 23 (a control) illustrates the use of potassium metal alcoholate as the catalyst. These data demonstrate the remarkable flexibility of operating conditions of which the present process is capable while still producing product having narrow molecular weight distribution, excellent overall properties and low levels of unreacted, residual alcohols.

TABLE I

Ethoxylation Catalysts by CaO Using MEEG "ACTIVATOR"
Preparation of Fatty Alcohol Ethoxylates Using CaO/MEEG As Catalyst System

| | \multicolumn{11}{c|}{Run No.} | |
|---|---|---|---|---|---|---|---|---|---|---|---|
| | 1 | 2 | 3 | 4 | 5 | 6 | 7 | 8 | 9 | 10 | 11 |
| REACTANTS, g. | | | | | | | | | | | |
| CaO[c] | 5* | 5* | 1* | 1* | 5* | 5* | 5 | 5* | 5* | 5* | 5* |
| MEEG | 300 | 300 | 300 | 300 | 300 | 300 | 300 | 300 | 300 | 300 | 300 |
| Fatty Alcohol | 500(D) | 500(D) | 500(L) | 500(L) | 500(L) | 500(L) | 500(L) | 500(L) | 500(L) | 500(L) | 500(L) |
| Acid Modifier (g.) | none | $H_2SO_4$(4.4) | $H_2SO_4$(0.1) | $H_2SO_4$(0.24) | $H_2SO_4$(2.1) | $H_2SO_4$(2.0) | $H_2SO_4$(0.88) | $H_2SO_4$(2.2) | $H_2SO_4$(0.87) | $H_2SO_4$(3.15) | $H_2SO_4$(2.7) |
| REACTION MODE | | | | | | | | | | | |
| Step 1[a] | M | M | M | C | C | C | C | C | M | C | C |
| Step 2[b] | — | AS | AS | AS | AS | AS | AS | BS | AS | AS | AS |
| REACTION CONDITIONS, STEP 1 | | | | | | | | | | | |
| Temp., °C. (Maximum) | 155 | 155 | 158 | 138 | 138 | 138 | 138 | 133 | 158 | 137 | 137 |
| Time, hours | 2 | 2 | 4 | 4 | 3.25 | 4 | 4 | 4.25 | 4.5 | 4 | 4 |
| MEEG | None | None | 29 | 30 | 34 | 23 | 18 | 41 | None | 27 | 16 |
| REACTION CONDITIONS, STEP 2 | | | | | | | | | | | |
| Temp., °C (maximum) | 215 | 214 | 222 | 223 | 223 | 224 | 224 | 223 | 227 | 223 | 224 |
| Pressure, mm Hg (minimum) | 180 | 155 | 180 | 180 | 180 | 180 | 180 | 155 | 200 | 180 | 180 |
| ETHOXYLATION CONDITIONS | | | | | | | | | | | |
| Temperature, °C. | 150–170 | 170 | 170 | 170–140 | 140 | 140 | 140 | 140 | 140 | 140 | 140 |
| Pressure, psig | 60 | 60 | 60 | 60 | 60 | 60 | 60 | 60 | 60 | 60 | 60 |
| Charge, g. | 472 | 481 | 434 | 382 | 426 | 425 | 428 | 473 | 439 | 451 | 444 |
| EO Added, g. | 776 | 804 | 620 | 540 | 602 | 598 | 604 | 666 | 620 | 1268 | 626 |
| Addition Time, min. | 266 | 303 | 390 | 310 | 117 | 162 | 168 | 296 | 223 | 142 | 89 |
| Rate, g./min. | 2.92 | 2.65 | 1.60 | 1.74 | 5.15 | 3.69 | 3.60 | 2.25 | 3.78 | 8.93 | 7.03 |
| ETHOXYLATE PROPERTIES | | | | | | | | | | | |
| Mol. wt. | 516 | 500 | — | — | — | 466.8 | — | 467.7 | — | — | 453.1 |
| Cloud Point, °C. | 64.5 | 54.5 | — | — | — | 48.5 | — | 48.5 | — | — | 45 |
| Ethoxylate No., Theo. on EO Add. | 6.95 | 7.06 | 6.58 | 6.82 | 6.52 | 6.50 | 6.51 | 6.50 | 6.52 | 13.10 | 6.50 |
| Area % Major Peak | 12.9 | 14.5 | — | — | — | 15.7 | 17.6 | 14.0 | — | — | 17.6 |
| Unreacted Alcohol, % (wt) | — | 3.01 | — | 1.74 | — | 1.79 | 3.60 | 3.66 | — | — | 1.72 |

| | \multicolumn{12}{c|}{Run No.} |
|---|---|---|---|---|---|---|---|---|---|---|---|---|
| | 12 | 13 | 14 | 15 | 16 | 17 | 18 | 19 | 20 | 21 | 22 | 23[g] |
| REACTANTS, g. | | | | | | | | | | | | |
| CaO[c] | (0.55) | 10* | None[e] | 0.28 | 10* | 10 | 10 | 10 | 10 | 9 | 9* | — |
| MEEG | | 600 | | | 600 | 600 | 600 | 600 | 1000(A) | 840 | 840 | — |
| Fatty Alcohol[f] | | 500(L) | | | 500(L) | 500(L) | 500(L) | 1000(A) | | 890(A) | 890(L) | 500(D) |
| Acid Modifier g. | | $H_2SO_4$ 0.42 | | | $H_2SO_4$(3.05) | $H_2SO_4$(3.05) | $H_3PO_4$(2.4) | $H_2SO_4$(2.67) | $H_3PO_4$(2.2) | $H_2SO_4$(3.05) | $H_2SO_4$(1.64) | — |
| REACTION MODE | | | | | | | | | | | | |
| Step 1[a] | | C | | | C | C | C | C | C | C | C | — |
| Step 2[b] | | AS | | | BS | BS | BS | BS | BS | BS | BS | — |
| REACTION CONDITIONS, STEP 1 | | | | | | | | | | | | |
| Temp., °C. (maximum) | | 136 | | | 136 | 136 | 136 | 137 | 135 | 135 | 135 | — |
| Time, hours | | 4 | | | 4 | 4 | 4 | 6.5 | 4.5 | 5 | 4 | — |
| MEEG Removed, g. | | 64 | | | 202 | 206 | 214 | 71.4 | 84 | 91 | 112 | — |

TABLE I-continued

Ethoxylation Catalysts by CaO Using MEEG "ACTIVATOR"
Preparation of Fatty Alcohol Ethoxylates Using CaO/MEEG As Catalyst System

| REACTION CONDITIONS STEP 2 | | | | | | | | | |
|---|---|---|---|---|---|---|---|---|---|
| Temp. °C. (maximum) | 225 | | 223 | 227 | 227 | 225 | 225 | 225 | 225 |
| Pressure, mm Hg (minimum) | 180 | | 180 | 180 | 180 | 190 | 190 | 190 | 190 |
| ETHOXYLATION CONDITIONS[c] | | | | | | | | | |
| Temperature, °C. | 140 | | 140 | 140 | 140 | 140 | 140 | 140 | 140 |
| Pressure, psig | 60 | | 60 | 60 | 60 | 60 | 60 | 60 | 60 |
| Charge, g | 452 | 439 | 466 | 472 | 432 | 465 | 466 | 780 | 478 | 490
| EO Added, g. | 638 | 618 | 654 | 664 | 606 | 636 | 670 | 1112 | 676 | 706
| Additional Time, min. | 123 | 131* | 82 | 71 | 339 | 126 | 201 | 170 | 96 | 85
| Rate, g./min | 5.19 | 3.18* | 7.98 | 9.35 | 1.79 | 4.68 | 3.33 | 6.54 | 7.62 | 8.31
| ETHOXYLATE PROPERTIES | | | | | | | | | |
| Mol. wt. | — | — | 473.0 | 493.1 | — | 506.3 | 476 | 497 | 482 | 458
| Cloud Point, °C. | — | — | 57 | 54 | — | 53 | 48 | 54 | 49 | 43
| Ethoxylate No. | | | | | | | | | |
| Theo. on EO Add. | 6.51 | 6.50 | 6.46 | 6.48 | 6.47 | 6.51 | 6.59 | 6.55 | 6.4 | 6.09
| Area % Major Peak | 19.7 | 21.5 | 18.6 | 17.1 | 27.6 | 18.1 | 22.5 | 17.4 | 18.6 | 10.4
| Unreacted Alcohol, % (wt) | — | — | 1.71 | 1.43 | — | 1.30 | 0.48 | 1.8 | 1.7 | 3.5

[a]Code for Step 1 reaction mode; M = mixture of MEEG and fatty alcohol, C = MEEG only present during initial reaction with CaO.
[b]Code for Step 2 reaction mode: BS = acid modifier added before stripping MEEG; AS = acid modifier added after stripping MEEG.
[c]Asterisk denotes CaO which was calcined 600° C./6 hours) before use.
[d]Master Batch - 1904 g. Lorol Special added to charge after stripping; divided into 4 × 471 g. portions, each of which was treated separately with H$_2$SO$_4$ as shown.
[e]Run 14 initially had no H$_2$SO$_4$ added; 0.43 g. H$_2$SO$_4$ was added after 5 hours of very slow ethoxylation reaction.
[f]Code for fatty alcohol; D = 1-dodecanol; L = Lorol 1214 Special; A = Alfol 1214.
[g]Comparative run using potassium metal as catalyst.

Example 2

As has been indicated above, the preferred procedure of this invention utilizes (a) the activator used alone in the initial reaction with CaO, (b) $H_2SO_4$ as the modifier, (c) the acid modifier added prior to removing the activator, and (d) the quantity of the acid being 50% of the "active" CaO content determined by the above-described titration at the end of the reflux period.

This version of the process was employed to prepare a series of surfactants by a sequential ethoxylation, wherein a single reactor charge was used and a portion of the reactor charge was used and a portion of the reactor contents was removed as each desired ethoxylation level was reached. Data for these runs are shown in Table II.

the larger major GC peak found in the ethoxylate produced with the CaO catalyst. Moreover, the residual alcohol content was substantially lower for the CaO catalyzed products.

The products of Runs 2, 3 and 7 were analyzed by capillary column gas chromatography and the following compositions were determined (error ±10% based on response factors for each specie).

| Composition | Run | | |
|---|---|---|---|
| (Wt. %) | 2 | 3 | 7 |
| n = 0 | 2.2 | 1.3 | 0.2 |
| 1 | 1.3 | 0.6 | 0.1 |
| 2 | 2.1 | 1.1 | 0.2 |
| 3 | 5.3 | 2.5 | 0.3 |
| 4 | 9.5 | 6.4 | 0.7 |
| 5 | 15.8 | 12.4 | 1.5 |
| 6 | 20.5 | 19.5 | 3.2 |
| 7 | 19.4 | 21.5 | 6.6 |
| 8 | 13.5 | 16.9 | 11.7 |
| 9 | 7.0 | 9.8 | 16.7 |
| 10 | 2.9 | 4.1 | 18.8 |
| 11 | 0.6 | 1.3 | 16.5 |
| 12 | — | 0.3 | 11.7 |
| 13 | — | — | 6.7 |
| 14 | — | — | 2.8 |
| 15 | — | — | 1.3 |
| 16 | — | — | 0.3 |

TABLE II

Ethoxylation Catalysis by CaO Using MEEG "ACTIVATOR"
Preparation of Surfactantg Products by Sequential Ethoxylation

| A. CATALYST PREPARATION | RUN 1 | RUN 2 |
|---|---|---|
| CHARGE, g. | | |
| CaO | 10 | 10 |
| MEEG | 600 | 600 |
| Alfol 1214 | 1000 | 1000 |
| $H_2SO_4$ | 2.66 | 3.61 |
| CONDITIONS | | |
| Step 1 | | |
| Temp., °C. (maximum) | 135 | 135 |
| Time, hrs | 4.5 | 4.1 |
| MEEG Removed, g. | 84 | 91 |
| Final Alkalinity, meq./g. | 0.107 | 0.129 |
| Step 2 | | |
| Temp., °C. (maximum) | 223 | 220 |
| Pressure, mm Hg | 190 | 190 |
| Final Alkalinity, meq./g. | 0.023 | 0.027 |

B. ETHOXYLATION

| Starter | Blend 49.3/50.7 Run 1/Run 2 |
|---|---|
| Charge, g. | 1800 |
| Temperature °C. | 140 |
| Pressure, psig | 60 |
| EO Added, g. | |

| To Product | 1 | 2 | 3 | 4 | 5 | 6 | 7 | 8 |
|---|---|---|---|---|---|---|---|---|
| | 1048 | 990 | 130 | 46 | 106 | 166 | 292 | 86 |
| Amt. of Product Removed, g. | 394 | 391 | 347 | 393 | 371 | 388 | 395 | 1491 |

C. ETHOXYLATE PROPERTIES

| | | | | | | | | |
|---|---|---|---|---|---|---|---|---|
| Mol. weight | 323 | 448 | 468 | 476 | 498 | 541 | 655 | 693 |
| Mols EO, Calc'd | 2.75 | 5.59 | 6.05 | 6.23 | 6.73 | 7.7 | 10.3 | 11.0 |
| Cloud Point, °C. | <20 | 37 | 46.5 | 50 | 60 | 73.5 | 94.5 | 99.5 |
| Major Component, Area % by GC | 21.7 | 20.5 | 19.6 | 20.8 | 20.7 | 21.2 | 22.8 | 22.8 |
| Unreacted Alcohol Content, Wt. % | 12.6 | 2.6 | 1.3 | 1.3 | 0.6 | 0.4 | — | 0.08 |

Example 3

A further series of sequential ethoxylation runs was performed in full-scale production facilities. Data for thse runs are summarized in Table III. In this table, "Ca" indicates the CaO-derived catalyst and "K" indicates control runs using KOH catalyst. It will be observed from these data that the CaO-derived catalyst produced a significantly narrower molecular weight disjtribution than the KOH catalyst, as evidenced by

TABLE III

Ethoxylation Catalysis by CaO Using MEEG "ACTIVATOR"
Commercial Scale Production of Surfactant Series by Sequential Ethoxylation
Using Both Ca and K Catalysts

| | RUN NO. | | | | | | | | | | | | | | | |
|---|---|---|---|---|---|---|---|---|---|---|---|---|---|---|---|---|
| | 1 | | 2 | | 3 | | 4 | | 5 | | 6 | | 7 | | 8 | |
| | Ca | K | Ca | K | Ca | K | Ca | K | Ca | K | Ca | K | Ca | K | Ca | K |
| Moles Ethylene Oxide per mole starter (nominal) | 3 | 3 | 5.8 | 6.2 | 6.2 | 6.6 | 6.5 | 6.4 | 6.9 | 7.3 | 8.5 | 9.0 | 10.5 | 10.9 | 11.0 | 11.5 |
| PROPERTIES: | | | | | | | | | | | | | | | | |
| Cloud Point, °C. | — | — | 32 | 34 | 44 | — | 49.1 | 51.0 | 62.6 | 58.8 | 72.4 | 72.7 | 91.0 | 92.2 | 97.0 | 96.0 |
| Hydroxyl No. | 177.5 | 169 | 124.7 | 121.1 | 120.2 | — | 112.9 | 111.7 | 106.9 | 107.1 | 96.3 | 97.5 | 83.4 | 84.4 | 78.3 | 80.4 |
| pH, 1% Solution | 7.1 | 6.5 | 4.5 | 5.1 | 4.8 | — | 5.1 | 5.1 | 4.4 | 5.0 | 3.9 | 5.3 | 4.3 | 5.7 | 3.8 | 6.5 |
| Water, Wt. % | 0.31 | 0.24 | 0.26 | 0.05 | 0.21 | — | 0.13 | 0.02 | 0.03 | 0.03 | 0.01 | 0.02 | 0.08 | 0.01 | 0.13 | 0.02 |
| Color, Pt/Co | 55 | 20 | 60 | 15 | 45 | — | 40 | 20 | 55 | 13 | 40 | 20 | 35 | 20 | 40 | 20 |
| PEG Content, %[a] | 0.87 | 0.03 | 1.16 | 0.49 | 1.46 | — | 1.21 | 0.51 | 1.44 | 0.61 | 1.43 | 0.55 | 1.76 | 0.6 | 1.9 | 1.76 |
| Unreacted Alcohol, % (QC) | 14.6 | 16.0 | 2.71 | 3.61 | 1.62 | — | 1.5 | 1.83 | 0.79 | 1.36 | 0.38 | 1.02 | 0.15 | 0.54 | 0.09 | 0.46 |
| Area % Major Peak | 17.4 | 12.7 | 18.2 | 9.9 | 19.8 | — | 18.1 | 11.1 | — | — | — | — | — | — | — | — |

[a]The PEG Content was determined using a solvent extraction technique for the recovery of lower molecular weight polyethylene glycols (PEG)

Example 4

As described above, the catalyst of this invention can be used not only in its "crude" form, as in the preceding examples, but can also be recovered and purified prior to use. This example illustrates the properties and use of the CaO-derived catalyst separated, purified and dried according to the techniques previously described. Table IV presents the key data for runs utilizing acid-modified vs. unmodified catalyst. For comparative purposes, appropriate data are given for a conventional potassium catalyst prepared by reacting potassium metal with 1-dodecanol. The latter is a homogeneous catalyst system and no attempt was made to isolate the active catalyst species. The dry CaO catalysts were obtained as yellow-colored, granular (rather lumpy) particulates which were too insoluble in MEEG or Alfol 1214 to yield a positive test for alkalinity. In fact, these solids formed such poor slurries in the Alfol 1214 added at the slurry preparation stage that, once again, no positive test for alkalinity was observable. (By "poor" slurry is meant that the solids could not be adequately suspended; i.e. the slurry was unstable and settled out within an hour or two). Characterization of these dry solids by reflectance IR, by powder X-ray, and by microanalysis indicated that the solids were X-ray amorphous, that some long-chain organic was present, that sulfur was present in the acid-modified species, and that unreacted CaO and Ca(OH)$_2$ were present in minor quantities.

As indicated by the ethoxylation rate data given in Table IV, both solids were low-activity catalysts despite their presence at quite substantial concentrations in the reactor charge. The unmodified catalyst, although present at a higher concentration than its acid-modified counterpart, exhibited poor activity at 140° C.; thus, the reactor temperature was increased to 160° C. in order to achieve reaction. The low levels of activity exhibited by the two CaO-based catalysts can be attributed to the very poor quality of the Alfol 1214 slurries obtained with the isolated catalyst species.

With Run No. 2, the intentional use of a less-than-optimum preparative procedure (CaO was heated with a mixture of MEEG and Alfol 1214 rather than with MEEG alone) probably also contributed to the relatively low catalyst activity. Under preferred preparative conditions where the catalyst is not isolated, activity levels from 3 to 6 times those observed in this study would be expected. The 7.1 g/min. rate shown in Table IV for the potassium-catalyzed (control) run is a typical value of KOH catalysis at 140° C. in the particular circulated loop reactor used to generate the data of these Examples. Thus, mechanical factors can be discounted as a possible cause of the relatively low activities obtained with the isolated version of the calcium catalysts.

Albeit the isolated, CaO-derived catalysts exhibited low activities, their performance characteristics were otherwise indistinguishable from those of their unisolated counterparts. Thus, while both CaO-based catalysts provided narrower molecular weight distribution ethoxylates than the potassium control catalyst, the acid-modified catalyst was not only more active than its unmodified counterpart, but also more selective as judged by comparisons of the molecular weight distribution patterns (narrower with acid-modified catalyst).

TABLE IV

Ethoxylation Catalysis By CaO Using MEEG "ACTIVATOR"
Use of Isolated (Dry) CaO/MEEG Catalysts
for Ethoxylation

| Run No. | 1 | 2 | 3[e] |
|---|---|---|---|
| ISOLATED CATALYST PREPARATION | | | |
| CHARGE, g. | | | |
| CaO | 5 | 5 | — |
| MEEG | 300[a] | 300[b] | — |
| Alfol 1214 | 500 | 500 | 500 |
| H$_2$SO$_4$ | 2.5 | None | — |
| K Metal | — | — | 1.15[d] |
| Dry Catalyst Yield, g. | 7.6 | 6.3 | n/a[e] |
| CATALYST SLURRY PREPARATION | | | |
| CHARGE, g. | | | |
| Dry Catalyst | 1.5 | 2.5 | — |
| Alfol 1214 | 500 | 500 | — |
| Wt. Removed in Stripping | 38.6 | 42 | — |
| ETHOXYLATION | | | |

TABLE IV-continued
Ethoxylation Catalysis By CaO Using MEEG "ACTIVATOR"
Use of Isolated (Dry) CaO/MEEG Catalysts
for Ethoxylation

| Run No. | 1 | 2 | 3[e] |
|---|---|---|---|
| CONDITIONS | | | |
| Catalyst Slurry g. | 450 | 450 | 488 |
| EO Added, g. | 632 | 634 | 692 |
| Time, min. | 323 | 1220 | 97 |
| Temp., °C. | 140 | 140–160 | 140 |
| Pressure, psig | 60 | 60 | 60 |
| Rate, g./min. | 1.96 | 0.52[c] | 7.13 |
| ETHOXYLATION PROPERTIES | | | |
| Cloud Point, °C. | 53 | 47.5 | 49 |
| pH | 5.3 | 6.4 | 4.8 |
| Hydroxyl No. | 114.02 | 114.82 | 117.49 |
| Mol. Weight | 492.0 | 488.6 | 477.5 |
| Moles EO Aver. | 6.96 | 6.88 | 6.63 |
| Area % Major CG Peak | 21.5 | 18.0 | 10.6 |
| Unreacted Alcohol, % | | | |
| Area | 2.9 | 3.4 | 6.5 |
| Weight | 0.81 | 0.87 | 2.54 |
| Summation Area %, Species $C_{12}{}^{-5}$ Through $C_{14}{}^{-7}$ | 53.79[f] | 49.84[f] | 31.45[f] |
| Position of Major Ethoxylate (mols EO) | 7 | 6 | 6,7 |

[a]MEEG alone used in initial reaction with CaO.
[b]Mixture of MEEG and Alfol 1214 used in initial reaction with CaO.
[c]Overall rate for reaction at both 140° C. and 160° C.
[d]Catalyst prepared by reacting potassium metal with Alfol 1214.
[e]Catalyst not isolated.
[f]All species from the $C_{12}{}^{-5}$ mol ethoxylate through $C_{14}{}^{-7}$ mol ethoxylate.

Example 5

This example depicts graphically the narrowed molecular weight distribution achieved by the process of this invention.

FIG. 1 shows typical molecular weight distributions for typical nominal 6-mol ethoxylates of 1-dodecanol made using CaO catalyst activated with ethylene glycol, acid-modified ethylene glycol (indicated by "H30"), MEEG acid-modified ethylenediamine (EDA) and monoethanolamine (MEA), all compared with a potassium metal control (prior art).

Figure 2:
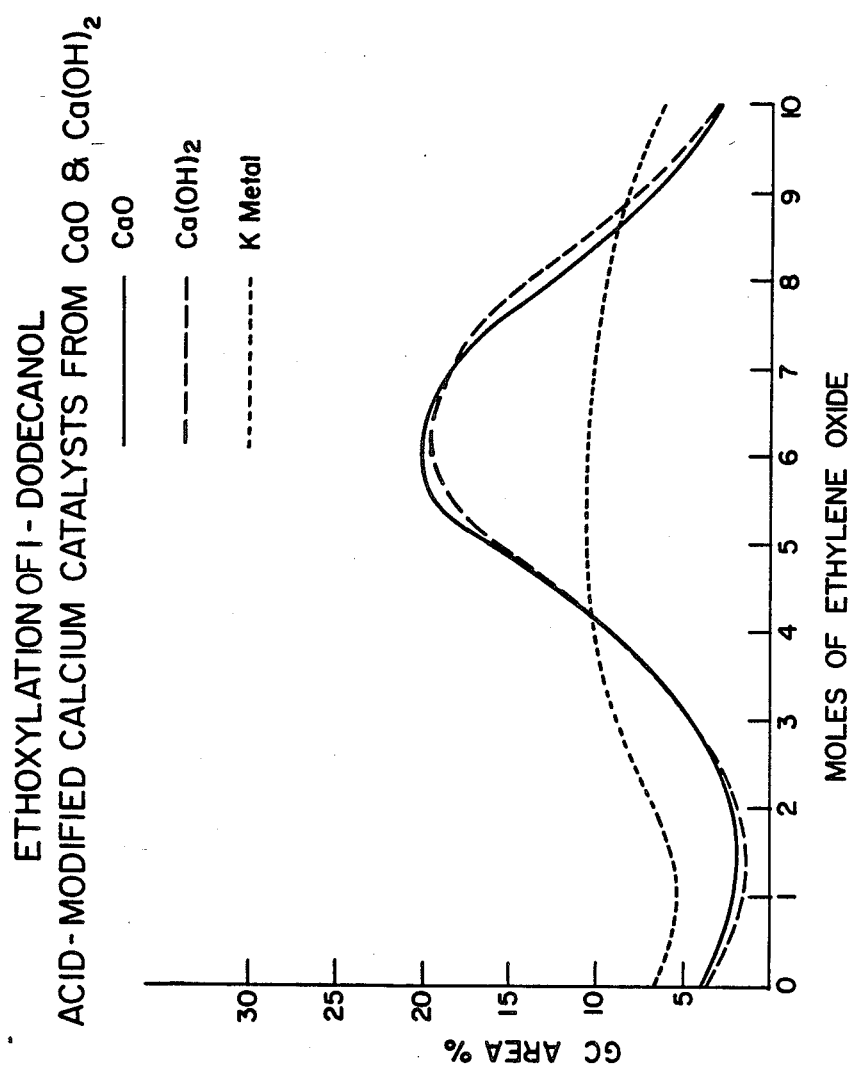

FIG. 2 provides a similar comparison and also demonstrates the practical equivalence in performance between CaO and Ca(OH)$_2$ using ethylene glycol as activator. It is a significant benefit of this invention that, since any contained or ambient moisture converts CaO to Ca(OH)$_2$, the invention is essentially insensitive to moisture present prior to alkoxylation.

Figure 3:
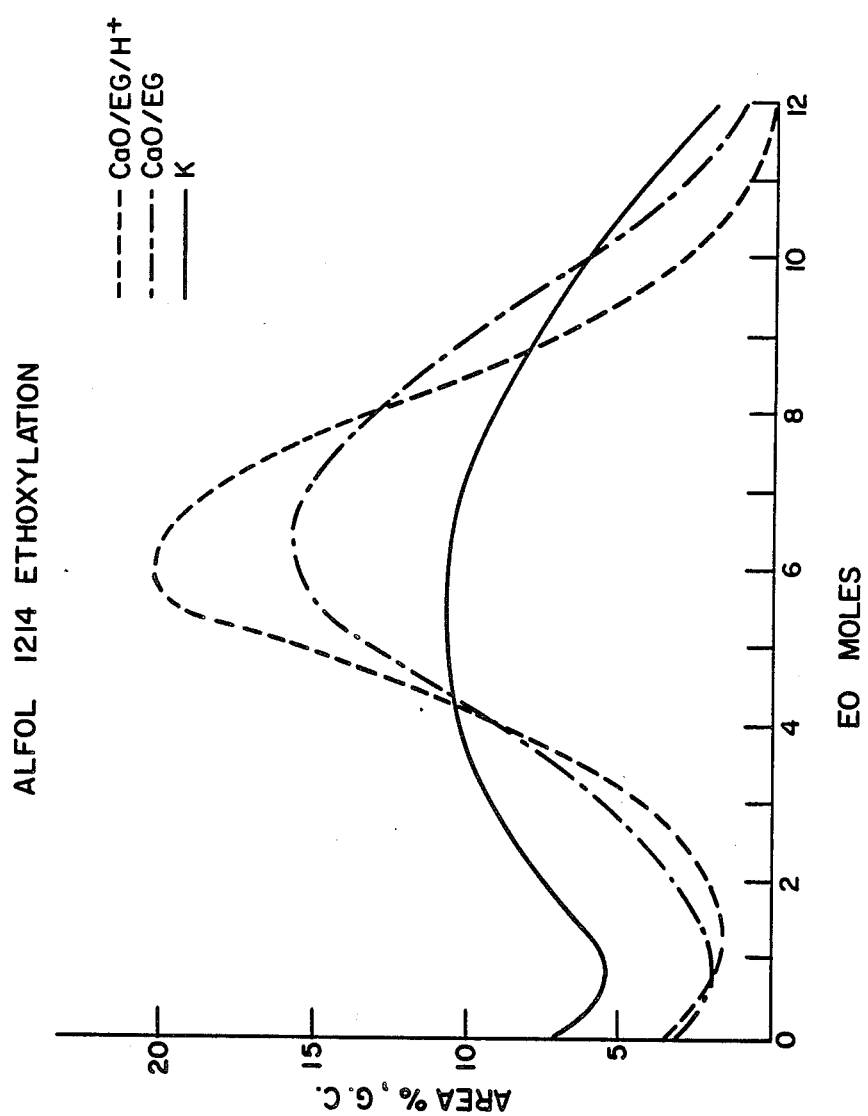

FIG. 3 illustrates ethoxylation of mixed surfactant-grade alcohols (Alfol 1214) using a CaO catalyst activated with ethylene glycol ("EG").

Similarly to FIG. 3, FIG. 4 shows the use of MEEG-activated CaO both unmodified and modified with either H$_3$PO$_4$ or H$_2$SO$_4$.

The distributions of the ethoxylates depicted in FIGS. 1 to 4 are determined using gas chromatography with a packed column of 2% OV-1 on Chromasorb W ™ packing. The temperature limit of the column is such that little accuracy is achieved with ethoxylates containing eight or more oxyethylene groups.

Example 6

Three batches of CaO and activator (monoethylene glycol) are prepared as follows:

Batch A: A mixing tank containing about 22,500 pounds (10,225 kg) of monoethylene glycol is sparged with nitrogen for about one hour at 45° to 50° C. The mixing tank is continuously agitated by means of a jet nozzle in the base of the tank and a spray ring at the top of the tank. Approximately 375 pounds (170 kg) of lime (CaO) is added to the mixing tank while the mixing tank is maintained under 500 mm Hg vacuum (about 0.34 atmospheres absolute) over a one-half hour period. The temperature of the fluid in the tank increased from about 48° C. to 59° C. during the addition of the lime. The mixing tank was then heated to about 118° C. (about 1.5 hours required to obtain the temperature) and then maintained at a temperature of about 118° to 130° C. for three hours.

About 400 pounds (182 kg) of dispersant, a surfactant made from a linear alcohol mixture of 12 to 14 carbons and three moles of ethylene oxide per mole of alcohol (available as TERGITOL ™ 24-L-3 (cmw) surfactant from Union Carbide Corporation) was added over a 1.5 hour period and during this time the temperature in the mixing tank dropped from about 127° C. to about 110°C. One hour after the dispersant addition was initiated, 37,500 pounds (17,050 kg) of alcohol (Alfol 1214) were added. The addition of the alcohol took about one hour at which time the temperature of the mixture was about 90° C. Upon the addition of the alcohol, a two-phase mixture formed and existed throughout the remainder of the preparation of this batch. The mixture was allowed to continue mixing for another 1.5 hours and then, over a one hour period, about 250 pounds (114 kg) of concentrated sulfuric acid were added. The mixture continued to be mixed for about 6.5 hours after the acid addition and was then pumped to a charge tank for later use. Each of the dispersant, alcohol and acid were added through the spray ring at the top of the mixing tank.

Batch B: Using the same mixing tank described above, except that only the bottom nozzle was used for mixing, a charge of 22,500 pounds (10,225 kg) of ethylene glycol is purged with nitrogen at about 45°–50° C. for one hour, 375 pounds (170 kg) of lime (CaO) were added under vacuum as in Batch A over a one-half hour period in approximately 50 pound (23 kg) segments during which time the temperature increased to about 62° C. Approximately 1.75 hours were required to heat the mixing tank to 116° C. and then the tank was maintained at about 116° to 130° C. for 2.5 hours. About 400 pounds (182 kg) of TERGITOL ™ 24-L-3 surfactant were added over a 0.75 hour period. About 0.75 hours after the dispersant had been added, 250 pounds (114 kg) of concentrated sulfuric acid were added over a one hour period. The mixing continued for about 2.5 hours and the reaction mixture, which was a single liquid-phase slurry, was then pumped to a circulated storage tank for subsequent use.

Batch C: The procedure and apparatus described for the preparation of Batch B were substantially repeated except that 400 pounds (182 kg) of lime were employed, the temperature of the ethylene glycol at the initiation of the addition of the lime was about 39° C. and the temperature rose to about 53° C., 300 pounds (136 kg) of concentrated sulfuric acid were employed, and after completion of the addition of the acid, the mixture was maintained at 90° C. for 3 hours prior to being sent to storage.

After preparing these three batches, Batch B and C were combined and admixed for about 20 hours. Alfol 1214 alcohol was added in lime as the mixture of Batches B and C was pumped to a distillation column. The distillation column has 24 valve (non-sealing) trays with 20 inch (50 centimeters) spacing and a nominal diameter of six feet (1.8 meters). The rate of addition of the alcohol was sufficient to provide a 5:3 weight ratio of the alcohol to ethylene glycol. The distillation column was operated as a stripping column with the feed (about 7000 to 9000 pounds per hour (3200 to 4000 kg per hour)) to the top tray of the column. The head temperature of the column was about 114° C. to 116° C. at about 33 to 35 mm Hg pressure absolute and the base was at about 205° to 215° C. The steam flow to the base was about 6000 to 7000 pounds per hour (2700 to 3200 kg per hour). The bottoms were removed periodically depending upon the liquid level in the column. The overhead make rate was about 3000 to 5000 pounds per hour (1400 to 2200 kg per hour). Batch A (with some additional Alfol 1214 to provide the 5:3 weight ratio) was then passed to the distillation column. The bottoms slurry from the batches were collected and stored in a circulated tank under a nitrogen atmosphere. Additional Alfol 1214 alcohol was added to the slurry to provide a concentration of catalyst (calculated as CaO) of 1.0 weight percent. This slurry was analyzed to contain about 0.1 weight percent ethylene glycol, evidencing that the stripping of ethylene glycol was not complete (less than 0.05 weight percent ethylene glycol is preferred).

This slurry, a master batch catalyst, served as the catalyst for a series of ethyoxylations of Alfol 1214 with ethylene oxide at 140° C. and pressure of 7 atmospheres gauge. The ethoxylation reactor was a 15,000 gallon capacity, circulated, nitrogen-inverted reactor. The starter and catalyst slurry (0.1 weight percent catalyst based on starter) was heated to 120° C. prior to initiating the flow of ethylene oxide. The ethylene oxide feed rate was initially about 3000 pounds per hour (1364 kg per hour) and increased to 9000 pounds per hour (4091 kg per hour) until about 100,000 pounds (45,454 kg) of ethoxylate were in the reactor. The residual ethylene oxide was reacted by holding the mixture at 140° C. for one hour. Sulfuric acid or phosphoric acid was used to neutralize the products which were filtered. The details of the runs are set forth in Table V.

TABLE V

| Elongation Condition | Run | | | | | |
|---|---|---|---|---|---|---|
| | 1 | 2 | 3 | 4 | 5 | 6 |
| Weight ratio of ED to | | | | | | |
| Alcohol | 0.66 | 0.22 | 1.14 | 1.42 | 1.52 | 2.55 |
| Composition of Ethoxylate, wt. %$^a$ | | | | | | |
| n=0$^b$ | 7.2 | 38.2 | 1.3 | 0.5 | 0.3 | — |
| 1 | 5.9 | 22.9 | 1.0 | 0.2 | 0.1 | — |
| 2 | 11.4 | 20.9 | 1.7 | 0.6 | 0.3 | — |
| 3 | 22.1 | 12.0 | 4.6 | 1.7 | 0.7 | — |
| 4 | 26.0 | 3.8 | 10.8 | 5.3 | 2.4 | 0.1 |
| 5 | 17.6 | 0.1 | 18.9 | 13.3 | 7.1 | 0.3 |
| 6 | 6.8 | — | 22.2 | 23.4 | 16.6 | 6.7 |
| 7 | 1.7 | — | 17.7 | 25.5 | 24.2 | 1.7 |
| 8 | 0.4 | — | 10.4 | 18.3 | 24.4 | 4.8 |
| 9 | 0.3 | — | 4.6 | 8.6 | 15.7 | 11.0 |
| 10 | 0.3 | — | 1.6 | 2.9 | 7.1 | 18.2 |
| 11 | 0.2 | — | 0.5 | 0.7 | 2.4 | 21.3 |
| 12 | 0.2 | — | 0.2 | 0.1 | 0.6 | 18.4 |
| 13 | — | — | 0.1 | — | 0.1 | 11.9 |
| 14 | — | — | — | — | — | 5.9 |
| 15 | — | — | — | — | — | 2.0 |
| 16 | — | — | — | — | — | — |

$^a$Determined by capillary column gas chromotography, error ± 10% based on response factors for specie.
$^b$number of oxyethylene groups in specie.

Example 7

This example illustrates procedures for preparing triethylene glycol (TEG) and tetraethylene glycol (TETEG) from ethylene glycol (EG).

The following general procedures were used for the runs. The calcium-containing catalyst was prepared at a temperature of 150° C. and pressure of about 180–200 mm Hg over a four hour period with continuous, slow removal of ethylene glycol overhead. Concentrated acid was used for modification and was added after the catalyst was admixed with the ethylene glycol for the ethoxylation (post addition) except as otherwise indicated. The ethoxylations were conducted at about 140° C. and 60 to 65 pounds per square inch gauge (about 4 atmospheres gauge) in a two gallon capacity circulated reactor. The mole ratio of ethylene oxide to ethylene glycol was 2.3:1. The charge to the reactor was about 500 grams of the ethylene glycol mixture. The products were neutralized at 80° C. with phosphoric acid and filtered hot though a Filter-Cal TM diatomaceous earth filter. Molecular weight distributions (area percent) were determined by gas chromatography using a packed column (2 percent OV-1 on Chromasorb W TM packing) and the samples were derivatized by reaction with Regisil TM silane available from the Regis Chemical Company. The details are provided in Table VI. In the Table, DEG represents diethylene glycol; PENTEG, pentylethylene glycol; and HEXAEG, hexaethylene glycol.

Example 8

This example illustrates procedures for preparing triethylene glycol and tetraethylene glycol from diethylene glycol.

The same general procedures as described in Example 7 were employed except that the catalyst activator was diethylene glycol and the pressure during the catalyst preparation was 40 mm Hg. The mole ratio of ethylene oxide to diethylene glycol was about 1.3:1. The details are provided in Table VII.

TABLE VI

| | Run: 1 | 2 | 3 | 4 | 5 | 6 | 7 | 8 | 9 |
|---|---|---|---|---|---|---|---|---|---|
| CONDITIONS: | | | | | | | | | |
| Procedure[a] | Std. | Std. | Std. | Std. | Std. | Non-Std.[b] | Std. | Non-Std.[c] | Std. |
| Catalyst | CaO | CaO | CaO | CaO | CaO | CaO | CaO | CaO | CaO |
| Catalyst Charge, g. | 1.01 | 1.10 | 1.0 | 1.04 | 1.0 | 1.0 | 1.0 | 2.0 | 1.0 |
| Catalyst Conc., Initial, % | 0.21 | 0.20 | 0.18 | 0.19 | 0.18 | 0.18 | 0.185 | 0.374 | 0.18 |
| Acid Modifier | None | $H_2SO_4$ | $H_2SO_4$ | Polyphos | $H_2SO_4$ | $H_2SO_4$ | $H_2SO_4$ | $H_2SO_4$ | $H_2SO_4$ |
| Modifier Charge, g. | — | 1.24 | 0.44 | 1.06 | 1.32 | 0.91 | 1.48 | 3.2 | 1.6 |
| Neutralization Level, % of Theory | 0 | 64.2 | 25.4 | 47.0 | 75.4 | 52.2 | 84.8 | 91.3 | 92.2 |
| Mol Ratio, EO/EG | | | | | | | | | |
| Target | 2.30 | 2.3 | 2.3 | 2.3 | 2.3 | 2.3 | 2.3 | 2.3 | 2.3 |
| Actual | 2.42 | 2.34 | 2.35 | 2.39 | 2.32 | 2.3 | 2.34 | 2.35 | 2.375 |
| PROPERTIES: | | | | | | | | | |
| Reaction Rate g./min. | 6.9 | 4.8 | 5.8 | 1.0 | 3.4 | 5.1 | 2.7 | 1.4 | 1.0 |
| Mol. Wght., by OH No. | 168.4 | 165.1 | 165.6 | 167.3 | 164.0 | 163.5 | 165.1 | 165.7 | 166.5 |
| Unreacted Starter, | | | | | | | | | |
| Area % | 6.5 | 3.6 | 4.8 | 4.5 | 2.8 | 5.0 | 3.7 | 3.8 | 4.1 |
| Wght. % | 5.1 | 2.7 | 3.4 | 3.5 | 1.8 | 3.6 | 2.5 | 2.8 | 3.5 |
| Distribution, Area %'s | | | | | | | | | |
| EG | 6.5 | 3.6 | 4.8 | 4.5 | 2.8 | 5.0 | 3.7 | 3.8 | 4.1 |
| DEG | 16.2 | 10.1 | 16.7 | 18.5 | 6.3 | 14.6 | 5.4 | 4.5 | 4.8 |
| TEG | 25.5 | 42.3 | 35.1 | 31.1 | 50.45 | 35.5 | 53.6 | 51.2 | 46.9 |
| TETEG | 29.4 | 30.0 | 29.8 | 27.1 | 30.8 | 29.2 | 29.0 | 30.7 | 31.1 |
| PENTEG | 14.5 | 10.5 | 11.2 | 12.9 | 8.5 | 11.7 | 7.0 | 8.5 | 10.6 |
| HEXAEG | 5.1 | 2.6 | 2.4 | 4.1 | 1.2 | 2.9 | 0.3 | 1.4 | 2.5 |
| >HEXAEG | 1.2 | 0.4 | — | 0.6 | — | 0.2 | — | — | — |

[a]Standard procedure means that modifier, if used, was post-added and that catalyst charge was nominal 1.0 g. CaO or its equivalency in. eg., KOH.
[b]Non-standard run because acid modifier was pre-added.
[c]Non-standard run because CaO catalyst charge was 2.0 g. rather than 1.0.

TABLE VII

| | Run: 1 | 2 | 3 | 4 | 5 | 6 | 7 | 8 | 9 | 10 | 11 |
|---|---|---|---|---|---|---|---|---|---|---|---|
| CONDITIONS: | | | | | | | | | | | |
| Procedure[a] | Std. | Non-std.[b] | Std. | Std. | Std. | Std. | Std. | Std. | Std. | Std. | Std. |
| Catalyst | CaO | CaO | CaO | CaO | CaO | KOH | CaO | CaO | CaO | CaO | CaO |
| Catalyst Charge, g. | 1.0 | 1.0 | 1.0 | 1.0 | 1.0 | 1.0[c] | 1.0 | 1.0 | 1.0 | 1.0 | 1.0 |
| Catalyst Conc., Initial, % | 0.18 | 0.18 | 0.18 | 0.18 | 0.18 | 0.18 | 0.18 | 0.18 | 0.18 | 0.18 | 0.18 |
| Acid Modifier | $H_2SO_4$ | $H_2SO_4$ | Oxalic | $H_2MoO_4$ | $H_2SO_4$ | None | $H_2SO_4$ | $H_2SO_4$ | $H_2SeO_4$ | $H_2WO_4$ | None |
| Modifier Charge, g. | 1.31 | 1.35 | 1.13 | 1.92 | 1.55 | — | 0.90 | 0.45 | 1.15 | 2.24 | — |
| Neutralization Level, % of Theory | 74.7 | 76.9 | 50.2 | 37.1 | 88.3 | — | 51.5 | 25.7 | 50.3 | 50.7 | — |
| Mol Ratio, EO/EG | | | | | | | | | | | |
| Target | 1.3 | 1.3 | 1.3 | 1.3 | 1.3 | 1.3 | 1.3 | 1.3 | 1.3 | 1.3 | 1.3 |
| Actual | 1.33 | 1.33 | 1.31 | 1.36 | 1.35 | 1.31 | 1.28 | 1.30 | 1.37 | 1.3 | 1.305 |
| PROPERTIES: | | | | | | | | | | | |
| Reaction Rate g./min. | 3.1 | 0.8 | 1.15 | 4.3 | 5.1 | 29.4 | 1.2 | 1.9 | 0.7 | 7.7 | 8.1 |
| Mol. Wght., by OH Mo. | 164.8 | 164.9 | 163.7 | 165.9 | 165.5 | 163.6 | 162.2 | 163.4 | 166.2 | 163.4 | 163.4 |
| Unreacted Starter, | | | | | | | | | | | |
| Area % | 3.1 | 10.6 | 18.9 | 17.75 | 4.2 | 18.6 | 5.5 | 17.4 | 16.5 | 19.4 | 19.5 |
| Wght. % | 2.1 | 7.6 | 12.5 | 12.6 | 3.1 | 12.9 | 3.2 | 12.4 | 10.95 | 13.6 | 12.7 |
| Distribution, Area %'s | | | | | | | | | | | |
| DEG | 3.1 | 10.6 | 18.9 | 17.75 | 4.1 | 18.6 | 5.5 | 17.4 | 16.7 | 19.4 | 19.5 |
| TEG | 61.3 | 51.3 | 40.1 | 40.7 | 60.1 | 39.8 | 58.8 | 38.9 | 38.2 | 36.2 | 34.3 |
| TETEG | 30.8 | 30.3 | 29.5 | 29.0 | 30.2 | 27.9 | 31.0 | 30.7 | 30.4 | 31.0 | 32.8 |
| PENTEG | 4.6 | 7.3 | 10.1 | 1.03 | 5.5 | 11.0 | 4.7 | 10.9 | 12.0 | 10.9 | 11.3 |
| HEXAEG | — | 0.5 | 1.5 | 1.9 | — | 2.7 | — | 2.0 | 2.8 | 2.4 | 2.1 |
| >HEXAEG | — | — | — | — | — | — | — | — | — | — | — |

[a]Standard procedure means that modifier, if used, was post-added and that catalyst charge was nominal 1.0 g. CaO or its equivalency in. eg., KOH, Ca(OH)$_2$.
[b]Non-standard run because acid modifier was pre-added to reaction system.
[c]KOH pellets, assay 85%.
[d]Laboratory reagent acid, ~85% concentration.
[e]Crystals in form of dihydrate.
[f]In form of MoO$_3$, or "89%" molybdic acid.

| | Run: 12 | 13 | 14 | 15 | 16 | 17 | 18 | 19 | 20 |
|---|---|---|---|---|---|---|---|---|---|
| CONDITIONS: | | | | | | | | | |
| Procedure[a] | Std. | Std. | Std. | Std. | Std. | Std. | Std. | Std. | Std. |
| Catalyst | CaO | CaO | CaO | CaO | CaO | CaO | CaO | CaO(OH)$_2$ | CaO |
| Catalyst Charge, g. | 1.0 | 1.0 | 1.0 | 1.0 | 1.0 | 1.0 | 1.0 | 1.31 | 1.0 |
| Catalyst Conc., Initial, % | 0.18 | 0.18 | 0.18 | 0.18 | 0.18 | 0.18 | 0.18 | 0.24 | 0.18 |
| Acid Modifier | $H_3PO_4$ | $H_3PO_4$ | $H_2WO_4$ | Oxalic | Terephthalic | $H_3SO_4$ | Oxalic | None | $H_2MoO_4$ |
| Modifier Charge, g. | 1.32[d] | 1.17[d] | 3.32 | 1.18[e] | 2.39 | 1.50 | 2.13[e] | — | 4.26[f] |

TABLE VII-continued

| | | | | | | | | | |
|---|---|---|---|---|---|---|---|---|---|
| Neutralization Level, % of Theory | 0 | 64.2 | 25.4 | 47.0 | 75.4 | 52.2 | 84.8 | 91.3 | 92.2 |
| Mol Ratio, EO/EG | | | | | | | | | |
| Target | 2.30 | 2.3 | 2.3 | 2.3 | 2.3 | 2.3 | 2.3 | 2.3 | 2.3 |
| Actual | 2.42 | 2.34 | 2.35 | 2.39 | 2.32 | 2.3 | 2.34 | 2.35 | 2.375 |
| PROPERTIES: | | | | | | | | | |
| Reaction Rate g./min. | 6.9 | 4.8 | 5.8 | 1.0 | 3.4 | 5.1 | 2.7 | 1.4 | 1.0 |
| Mol. Wght., by OH No. | 168.4 | 165.1 | 165.6 | 167.3 | 164.0 | 163.5 | 165.1 | 165.7 | 166.5 |
| Unreacted Starter, | | | | | | | | | |
| Area % | 6.5 | 3.6 | 4.8 | 4.5 | 2.8 | 5.0 | 3.7 | 3.8 | 4.1 |
| Wght. % | 5.1 | 2.7 | 3.4 | 3.5 | 1.8 | 3.6 | d 2.5 | 2.8 | 3.5 |
| Distribution, Area %'s | | | | | | | | | |
| EG | 6.5 | 3.6 | 4.8 | 4.5 | 2.8 | 5.0 | 3.7 | 3.8 | 4.1 |
| DEG | 16.2 | 10.1 | 16.7 | 18.5 | 6.3 | 14.6 | 5.4 | 4.5 | 4.8 |
| TEG | 25.5 | 42.3 | 35.1 | 31.1 | 50.45 | 35.5 | 53.6 | 51.2 | 46.9 |
| TETEG | 29.4 | 30.0 | 29.8 | 27.1 | 30.8 | 29.2 | 29.0 | 30.7 | 31.1 |
| PENTEG | 14.5 | 10.5 | 11.2 | 12.9 | 8.5 | 11.7 | 7.0 | 8.5 | 10.6 |
| HEXAEG | 5.1 | 2.6 | 2.4 | 4.1 | 1.2 | 2.9 | 0.3 | 1.4 | 2.5 |
| >HEXAEG | 1.2 | 0.4 | — | 0.6 | — | 0.2 | — | — | — |

<sup>a</sup>Standard procedure means that modifier, if used, was post-added and that catalyst charge was nominal 1.0 g. CaO or its equivalency in. eg., KOH.
<sup>b</sup>Non-standard run because acid modifier was pre-added.
<sup>c</sup>Non-standard run because CaO catalyst charge was 2.0 g. rather than 1.0.

It is claimed:

1. An alkoxylation product mixture resulting from the reaction of an organic compound having at least one active hydrogen with an epoxide in which the mole ratio of reacted epoxide per active hydrogen is at least about 4 characterized by having at least one alkoxylation moiety which constitutes about 20 to 40 weight percent of the mixture; the weight percent of the mixture having three or more oxyalkylene units than the average peak alkoxylation specie is less than about 12 weight percent of the mixture; the alkoxylation specie having one oxyalkylene group more than that of the most prevalent specie and the alkoxylation specie having one oxyalkylene group less than that of the most prevalent specie are present in a weight ratio to the most prevalent specie of about 0.6:1 to 1:1.

2. The product mixture of claim 1 in which the alkoxylation species falling within the range of the weight average alkoxylation number plus or minus two comprise between about 80 and 95 weight percent of the mixture.

3. The product mixture of claim 2 wherein the oxyalkylene groups comprise oxyethylene.

4. The product mixture of claim 2 in which the mole ratio of epoxide reacted to active hydrogens is about 4 to 16.

5. The product mixture of claim 4 in which the organic compound having the active hydrogen is an alcohol.

6. The product mixture of claim 5 in which the alcohol comprises monohydric, aliphatic alcohol having about 8 to 20 carbons.

7. The product mixture of claim 6 in which the most prevalent alkoxylation specie has 6, 7, 8, 9, 10, 11 or 12 oxyalkylene units.

8. An alkoxylation product mixture resulting from the reaction of an alcohol with an epoxide have an alkoxylation specie distribution corresponding to the formula $$P_n = A \times e^{-(n-\bar{n})/2.6 + 0.4n}$$

wherein n is an integer of at least one and is the number of oxyalkylene groups per reactive hydrogen site of the alcohol for the alkoxylation specie, $\bar{n}$ is the weight average oxyalkylene number of the mixture, A is the weight percent of the most prevalent alkoxylation specie in the mixture and $P_n$ is, within plus or minus two percentage points, the weight percent of the alkoxylation specie having n oxyalkylene groups per active hydrogen site, based on the weight of the mixture.

9. The product mixture of claim 8 in which the most prevalent alkoxylation specie has 6, 7, 8, 9, 10, 11 or 12 oxyalkylene units.

10. The product mixture of claim 9 in which the alcohol comprises dihydric alcohol.

11. The product mixture of claim 10 in which the dihydric alcohol comprises ethylene glycol.

12. The product mixture of claim 11 in which the epoxide comprises ethylene oxide.

13. The product mixture of claim 9 in which the alcohol comprises monohydric, aliphatic alcohol of about 8 to 20 carbon atoms.

14. The product mixture of claim 13 in which the epoxide comprises ethylene oxide.

15. The product mixture of claim 14 in which at least one alkoxylation specie comprises about 22 to 28 weight percent of the composition.

16. The product mixture of claim 15 in which the most prevalent alkoxylation specie has 6, 7 or 8 oxyalkylene groups.

17. The product mixture of claim 2 wherein the oxyalkylene groups comprise oxyethylene and oxypropylene.

18. The product mixture of claim 16 in which the alcohol comprises a monohydric, aliphatic alcohol having from 1 to 7 carbons.

19. The product mixture of claim 5 in which the alcohol comprises dihydric alcohol.

20. The product mixture of claim 19 in which the dihydric alcohol is ethylene glycol.

21. The product mixture of claim 5 in which the alcohol comprises polyhydric alcohol.

22. The product mixture of claim 21 in which the polyhydric alcohol is glycerine.

23. The product mixture of claim 6 in which the alcohol is selected from n-dodecanol, a mixture of $C_8$–$C_{10}$ alcohols or a mixture of $C_{12}$–$C_{14}$ alcohols.

24. The product mixture of claim 8 wherein the epoxide is ethylene oxide.

25. The product mixture of claim 8 wherein the epoxide is ethylene oxide and propylene oxide.

26. The product mixture of claim 8 in which the alcohol comprises a monohydric, aliphatic alcohol having from 1 to 7 carbon atoms.

27. The product mixture of claim 8 in which the alcohol comprises a polyhydric alcohol.

28. The product mixture of claim 27 in which the polyhydric alcohol is glycerine.

29. The product mixture of claim 13 in which the alcohol is selected from n-dodecanol, a mixture of $C_8$–$C_{10}$ alcohols or a mixture of $C_{12}$–$C_{14}$ alcohols.

30. An alkoxylation product mixture resulting from the reaction of a monohydric, aliphatic alcohol of about 8 to 20 carbon atoms with ethylene oxide and/or propylene oxide having an alkoxylation specie distribution corresponding to the formula $$P_n = A \times e^{-(n-\bar{n})/2.6 + 0.4n}$$

wherein n is an integer of at least one and is the number of oxyalkylene groups per reactive hydrogen site of the alcohol for the alkoxylation specie, $\bar{n}$ is the weight average oxyalkylene number of the mixture, A is the weight percent of the most prevalent alkoxylation specie in the mixture in which said most prevalent alkoxylation specie has 6, 7, 8, 9, 10, 11 or 12 oxyalkylene units and $P_n$ is, within plus or minus two percentage points, the weight percent of the alkoxylation specie having n oxyalkylene groups per active hydrogen site, based on the weight of the mixture.

31. An alkoxylation product mixture resulting from the reaction of a monohydric, aliphatic alcohol of about 1 to 7 carbon atoms with ethylene oxide and/or propylene oxide having an alkoxylation specie distribution corresponding to the formula $$P_n = A \times e^{-(n-\bar{n})/2.6 + 0.4n}$$

wherein n is an integer of at least one and is the number of oxyalkylene groups per reactive hydrogen site of the alcohol for the alkoxylation specie, $\bar{n}$ is the weight average oxyalkylene number of the mixture, A is the weight percent of the most prevalent alkoxylation specie in the mixture in which said most prevalent alkoxylation specie has 6, 7, 8, 9, 10, 11 or 12 oxyalkylene units and $P_n$ is, within plus or minus two percentage points, the weight percent of the alkoxylation specie having n oxyalkylene groups per active hydrogen site, based on the weight of the mixture.

* * * * *

UNITED STATES PATENT AND TRADEMARK OFFICE
CERTIFICATE OF CORRECTION

PATENT NO. : 4,886,917

DATED : December 12, 1989

INVENTOR(S) : Robert J. Knopf et al.

It is certified that error appears in the above-identified patent and that said Letters Patent is hereby corrected as shown below:

Column 4, lines 45-46, that portion reading "catalysts" should read -- catalysis --.

Column 5, line 35, that portion reading "10" should read -- 19 --.

Column 6, line 17, that portion reading "envionmentally" should read -- environmentally -- .

Column 8, line 23, that portion reading "by by" should read -- by --.

Column 8, line 31, that portion reading "thevalency" should read -- the valency --.

Column 11, line 17, that portion reading "applicatin" should read -- application --.

Column 11, line 52, that portion reading "wit" should read -- with --.

Column 12, line 68, that portion reading "reagard" should read -- regard --.

Column 24, line 6, that portion reading "aserisk" should read -- asterisk --.

Column 29, line 62, that portion reading "thse" should read -- these --.

Column 29, line 67, that portion reading "disjtribution" should read -- distribution --.

UNITED STATES PATENT AND TRADEMARK OFFICE
CERTIFICATE OF CORRECTION

PATENT NO. : 4,886,917

DATED : December 12, 1989

INVENTOR(S) : Robert J. Knopf et al.

It is certified that error appears in the above-identified patent and that said Letters Patent is hereby corrected as shown below:

Column 33, line 46, that portion reading "$H^{30}$" should read -- $H^+$ --.

Columns 37 and 38, Table VI, Acid Modifier under Run 4, that portion reading "polyphos" should read -- polyphosphoric --.

Columns 37 and 38, Table VII, Acid Modifier under Run 4, that portion reading "$H_2MoO_4$" should read -- $H_2MoO_4 f$ --.

Columns 37 and 38, Table VII, Area % of Unreacted Starter under Run 9, that portion reading "16.5" should read -- 16.7 --.

Column 40, line 57, that portion reading "claim 16" should read -- claim 5 --.

Signed and Sealed this

Fourth Day of December, 1990

Attest:

HARRY F. MANBECK, JR.

*Attesting Officer*   *Commissioner of Patents and Trademarks*